US006368395B1

(12) United States Patent
Nohr et al.

(10) Patent No.: US 6,368,395 B1
(45) Date of Patent: Apr. 9, 2002

(54) SUBPHTHALOCYANINE COLORANTS, INK COMPOSITIONS, AND METHOD OF MAKING THE SAME

(75) Inventors: Ronald Sinclair Nohr, Alpharetta; John G. MacDonald, Decatur, both of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/569,549

(22) Filed: May 12, 2000

Related U.S. Application Data
(60) Provisional application No. 60/135,456, filed on May 24, 1999, and provisional application No. 60/175,653, filed on Jan. 12, 2000.

(51) Int. Cl.$^7$ .................. C09D 11/00; C07D 209/04; C07F 5/02
(52) U.S. Cl. .............. 106/31.47; 106/31.78; 106/410; 548/110; 548/405; 546/13
(58) Field of Search ............ 106/31.49, 31.73, 106/410; 548/405, 110; 546/13

(56) References Cited

U.S. PATENT DOCUMENTS

| | | | |
|---|---|---|---|
| 575,228 A | 1/1897 | von Gallois |
| 582,853 A | 5/1897 | Feer |
| 893,636 A | 7/1908 | Maywald |
| 1,013,544 A | 1/1912 | Fuerth |
| 1,325,971 A | 12/1919 | Akashi |
| 1,364,406 A | 1/1921 | Olsen |
| 1,436,856 A | 11/1922 | Brenizer et al. |
| 1,744,149 A | 1/1930 | Staehlin |
| 1,803,906 A | 5/1931 | Krieger et al. |
| 1,844,199 A | 2/1932 | Bicknell et al. |
| 1,876,880 A | 9/1932 | Drapal |
| 1,880,572 A | 10/1932 | Wendt et al. |
| 1,880,573 A | 10/1932 | Wendt et al. |
| 1,916,350 A | 7/1933 | Wendt et al. |
| 1,916,779 A | 7/1933 | Wendt et al. |
| 1,955,898 A | 4/1934 | Wendt et al. |
| 1,962,111 A | 6/1934 | Bamberger |
| 2,005,378 A | 6/1935 | Kiel |
| 2,005,511 A | 6/1935 | Stoll et al. |
| 2,049,005 A | 7/1936 | Gaspar |
| 2,054,390 A | 9/1936 | Rust et al. |
| 2,058,489 A | 10/1936 | Murch et al. |
| 2,062,304 A | 12/1936 | Gaspar |
| 2,090,511 A | 8/1937 | Crossley et al. |
| 2,097,119 A | 10/1937 | Eggert |
| 2,106,539 A | 1/1938 | Schnitzspahn |
| 2,111,692 A | 3/1938 | Saunders et al. |
| 2,125,015 A | 7/1938 | Gaspar |
| 2,130,572 A | 9/1938 | Wendt |
| 2,132,154 A | 10/1938 | Gaspar |
| 2,145,960 A | 2/1939 | Wheatley et al. |
| 2,154,996 A | 4/1939 | Rawling |
| 2,159,280 A | 5/1939 | Mannes et al. |
| 2,171,976 A | 9/1939 | Erickson |
| 2,181,800 A | 11/1939 | Crossley et al. |
| 2,185,153 A | 12/1939 | Lecher et al. |
| 2,220,178 A | 11/1940 | Schneider |
| 2,230,590 A | 2/1941 | Eggert et al. |
| 2,237,885 A | 4/1941 | Markush et al. |
| 2,243,630 A | 5/1941 | Houk et al. |
| 2,268,324 A | 12/1941 | Polgar |
| 2,281,895 A | 5/1942 | van Poser et al. |
| 2,328,166 A | 8/1943 | Poigar et al. |
| 2,346,090 A | 4/1944 | Staehle |
| 2,349,090 A | 5/1944 | Haddock |
| 2,356,618 A | 8/1944 | Rossander et al. |
| 2,361,301 A | 10/1944 | Libby, Jr. et al. |
| 2,364,359 A | 12/1944 | Kienle et al. |
| 2,381,145 A | 8/1945 | von Glahn et al. |
| 2,382,904 A | 8/1945 | Federsen |
| 2,386,646 A | 10/1945 | Adams et al. |
| 2,402,106 A | 6/1946 | von Glahn et al. |
| 2,416,145 A | 2/1947 | Biro |
| 2,477,165 A | 7/1949 | Bergstrom |
| 2,527,347 A | 10/1950 | Bergstrom |
| 2,580,461 A | 1/1952 | Pearl |
| 2,601,669 A | 6/1952 | Tullsen |
| 2,612,494 A | 9/1952 | von Glahn et al. |
| 2,612,495 A | 9/1952 | von Glahn et al. |
| 2,628,959 A | 2/1953 | von Glahn et al. |
| 2,647,080 A | 7/1953 | Joyce |
| 2,680,685 A | 6/1954 | Ratchford |
| 2,728,784 A | 12/1955 | Tholstrup et al. |

(List continued on next page.)

FOREIGN PATENT DOCUMENTS

| AU | 103085 | 4/1937 |
| AU | 12624/88 | 9/1988 |
| BE | 620075 | 5/1962 |

(List continued on next page.)

OTHER PUBLICATIONS del Ray, B. et al., "Synthesis and Nonlinear Optical, Photophysical, and Electrochemical Properties of Subphthalocyanines," J. Amer. Chem. Soc., vol. 120, pp. 12808–12817 (1998), no month available.

(List continued on next page.)

Primary Examiner—Helene Klemanski
(74) Attorney, Agent, or Firm—Kilpatrick Stockton LLP

(57) ABSTRACT

The present invention is directed to methods of making subphthalocyanine compounds. The methods of the present invention may be used to produce known subphthalocyanine compounds, as well as, a new family of subphthalocyanine compounds. The methods of the present invention may employ environmentally-friendly solvents, which donate a hydrogen atom for use in the reaction mechanism. The methods of the present invention produce subphthalocyanine compounds at a yield of greater than about 50%, and even greater than about 94%. The present invention is further directed to subphthalocyanine compounds having improved lightfastness. The subphthalocyanine compounds may have a Subphth-Lightfastness Test Value of less than 15%.

29 Claims, No Drawings

U.S. PATENT DOCUMENTS

| | | |
|---|---|---|
| 2,732,301 A | 1/1956 | Robertson et al. |
| 2,744,103 A | 5/1956 | Koch |
| 2,757,090 A | 7/1956 | Meugebauer et al. |
| 2,763,550 A | 9/1956 | Lovick |
| 2,768,171 A | 10/1956 | Clarke et al. |
| 2,773,056 A | 12/1956 | Helfaer |
| 2,798,000 A | 7/1957 | Monterman |
| 2,809,189 A | 10/1957 | Stanley et al. |
| 2,827,358 A | 3/1958 | Kaplan et al. |
| 2,834,773 A | 5/1958 | Scalera et al. |
| 2,875,045 A | 2/1959 | Lurie |
| 2,892,865 A | 6/1959 | Giraldi et al. |
| 2,897,187 A | 7/1959 | Koch |
| 2,936,241 A | 5/1960 | Sharp et al. |
| 2,940,853 A | 6/1960 | Sagura et al. |
| 2,955,067 A | 10/1960 | McBurney et al. |
| 2,992,129 A | 7/1961 | Gauthier |
| 2,992,198 A | 7/1961 | Funahashi |
| 3,030,208 A | 4/1962 | Schellenberg et al. |
| 3,071,815 A | 1/1963 | MacKinnon |
| 3,075,014 A | 1/1963 | Palopoli et al. |
| 3,076,813 A | 2/1963 | Sharp |
| 3,104,973 A | 9/1963 | Sprague et al. |
| 3,114,634 A | 12/1963 | Brown et al. |
| 3,121,632 A | 2/1964 | Sprague et al. |
| 3,123,647 A | 3/1964 | Duennenberger et al. |
| 3,133,049 A | 5/1964 | Hertel et al. |
| 3,140,949 A | 7/1964 | Sprague et al. |
| 3,154,416 A | 10/1964 | Fidelman |
| 3,155,509 A | 11/1964 | Roscow |
| 3,175,905 A | 3/1965 | Wiesbaden |
| 3,178,285 A | 4/1965 | Anderau et al. |
| 3,238,163 A | 3/1966 | O'Neill |
| 3,242,215 A | 3/1966 | Heitmiller |
| 3,248,337 A | 4/1966 | Zirker et al. |
| 3,266,973 A | 8/1966 | Crowley |
| 3,282,886 A | 11/1966 | Gadecki |
| 3,284,205 A | 11/1966 | Sprague et al. |
| 3,300,314 A | 1/1967 | Rauner et al. |
| 3,304,297 A | 2/1967 | Wegmann et al. |
| 3,305,361 A | 2/1967 | Gaynor et al. |
| 3,313,797 A | 4/1967 | Kissa |
| 3,320,080 A | 5/1967 | Mazzarella et al. |
| 3,330,659 A | 7/1967 | Wainer |
| 3,341,492 A | 9/1967 | Champ et al. |
| 3,359,109 A | 12/1967 | Harder et al. |
| 3,361,827 A | 1/1968 | Biletch |
| 3,363,969 A | 1/1968 | Brooks |
| 3,385,700 A | 5/1968 | Willems et al. |
| 3,397,984 A | 8/1968 | Williams et al. |
| 3,415,875 A | 12/1968 | Luethi et al. |
| 3,418,118 A | 12/1968 | Thommes et al. |
| 3,445,234 A | 5/1969 | Cescon et al. |
| 3,453,258 A | 7/1969 | Parmerter et al. |
| 3,453,259 A | 7/1969 | Parmerter et al. |
| 3,464,841 A | 9/1969 | Skofronick |
| 3,467,647 A | 9/1969 | Benninga |
| 3,479,185 A | 11/1969 | Chambers |
| 3,488,269 A | 1/1970 | Allen et al. |
| 3,502,476 A | 3/1970 | Kohei et al. |
| 3,503,744 A | 3/1970 | Itano et al. |
| 3,514,597 A | 5/1970 | Haes et al. |
| 3,541,142 A | 11/1970 | Cragoe, Jr. |
| 3,546,161 A | 12/1970 | Wolheim |
| 3,547,646 A | 12/1970 | Hori et al. |
| 3,549,367 A | 12/1970 | Chang et al. |
| 3,553,710 A | 1/1971 | Lloyd et al. |
| 3,563,931 A | 2/1971 | Horiguchi |
| 3,565,753 A | 2/1971 | Yurkowitz |
| 3,574,624 A | 4/1971 | Reynolds et al. |
| 3,579,533 A | 5/1971 | Yalman |
| 3,595,655 A | 7/1971 | Robinson et al. |
| 3,595,657 A | 7/1971 | Robinson et al. |
| 3,595,658 A | 7/1971 | Gerlach et al. |
| 3,595,659 A | 7/1971 | Gerlach et al. |
| 3,607,639 A | 9/1971 | Krefeld et al. |
| 3,607,693 A | 9/1971 | Heine et al. |
| 3,607,863 A | 9/1971 | Dosch |
| 3,615,562 A | 10/1971 | Harrison et al. |
| 3,617,288 A | 11/1971 | Hartman et al. |
| 3,617,335 A | 11/1971 | Kumura et al. |
| 3,619,238 A | 11/1971 | Kimura et al. |
| 3,619,239 A | 11/1971 | Osada et al. |
| 3,637,337 A | 1/1972 | Pilling |
| 3,637,581 A | 1/1972 | Horioguchi et al. |
| 3,642,472 A | 2/1972 | Mayo |
| 3,647,467 A | 3/1972 | Grubb |
| 3,652,275 A | 3/1972 | Baum et al. |
| 3,660,542 A | 5/1972 | Adachi et al. |
| 3,667,954 A | 6/1972 | Itano et al. |
| 3,668,188 A | 6/1972 | King et al. |
| 3,669,925 A | 6/1972 | King et al. |
| 3,671,096 A | 6/1972 | Mackin |
| 3,671,251 A | 6/1972 | Houle et al. |
| 3,676,690 A | 7/1972 | McMillin et al. |
| 3,678,044 A | 7/1972 | Adams |
| 3,689,565 A | 9/1972 | Hoffmann et al. |
| 3,694,241 A | 9/1972 | Guthrie et al. |
| 3,695,879 A | 10/1972 | Laming et al. |
| 3,697,280 A | 10/1972 | Strilko |
| 3,705,043 A | 12/1972 | Zablak |
| 3,707,371 A | 12/1972 | Files |
| 3,729,313 A | 4/1973 | Smith |
| 3,737,628 A | 6/1973 | Azure |
| 3,765,896 A | 10/1973 | Fox |
| 3,775,130 A | 11/1973 | Enomoto et al. |
| 3,788,849 A | 1/1974 | Taguchi et al. |
| 3,799,773 A | 3/1974 | Watarai et al. |
| 3,800,439 A | 4/1974 | Sokolski et al. |
| 3,801,329 A | 4/1974 | Sandner et al. |
| 3,817,752 A | 6/1974 | Laridon et al. |
| 3,840,338 A | 10/1974 | Zviak et al. |
| 3,844,790 A | 10/1974 | Chang et al. |
| RE28,225 E | 11/1974 | Heseltine et al. |
| 3,870,524 A | 3/1975 | Watanabe et al. |
| 3,873,500 A | 3/1975 | Kato et al. |
| 3,876,496 A | 4/1975 | Lozano |
| 3,887,450 A | 6/1975 | Gilano et al. |
| 3,895,949 A | 7/1975 | Akamatsu |
| 3,901,779 A | 8/1975 | Mani |
| 3,904,562 A | 9/1975 | Hopfenberg et al. |
| 3,910,993 A | 10/1975 | Avar et al. |
| 3,914,165 A | 10/1975 | Gaske |
| 3,914,166 A | 10/1975 | Rudolph et al. |
| 3,915,824 A | 10/1975 | McGinniss |
| 3,919,323 A | 11/1975 | Houlihan et al. |
| 3,926,641 A | 12/1975 | Rosen |
| 3,928,264 A | 12/1975 | Young, Jr. et al. |
| 3,933,682 A | 1/1976 | Bean |
| RE28,789 E | 4/1976 | Chang |
| 3,952,129 A | 4/1976 | Matsukawa et al. |
| 3,960,685 A | 6/1976 | Sano et al. |
| 3,965,157 A | 6/1976 | Harrison |
| 3,978,132 A | 8/1976 | Houlihan et al. |
| 3,984,248 A | 10/1976 | Sturmer |
| 3,988,154 A | 10/1976 | Sturmer |
| 4,004,998 A | 1/1977 | Rosen |
| 4,012,256 A | 3/1977 | Levinos |
| 4,017,652 A | 4/1977 | Gruber |
| 4,022,674 A | 5/1977 | Rosen |
| 4,024,324 A | 5/1977 | Sparks |

| | | |
|---|---|---|
| 4,039,332 A | 8/1977 | Kokelenberg et al. |
| 4,043,819 A | 8/1977 | Baumann |
| 4,048,034 A | 9/1977 | Martan |
| 4,054,719 A | 10/1977 | Cordes, III |
| 4,056,665 A | 11/1977 | Tayler et al. |
| 4,058,400 A | 11/1977 | Crivello |
| 4,067,892 A | 1/1978 | Thorne et al. |
| 4,071,424 A | 1/1978 | Dart et al. |
| 4,073,968 A | 2/1978 | Miyamoto et al. |
| 4,077,769 A | 3/1978 | Garcia |
| 4,079,183 A | 3/1978 | Green |
| 4,085,062 A | 4/1978 | Virgilio et al. |
| 4,090,877 A | 5/1978 | Streeper |
| 4,100,047 A | 7/1978 | McCarty |
| 4,105,572 A | 8/1978 | Gorondy |
| 4,107,733 A | 8/1978 | Schickedanz |
| 4,110,112 A | 8/1978 | Roman et al. |
| 4,111,699 A | 9/1978 | Krueger |
| 4,114,028 A | 9/1978 | Baio et al. |
| 4,126,412 A | 11/1978 | Masson et al. |
| 4,132,562 A | 1/1979 | Burke, Jr. et al. |
| 4,141,807 A | 2/1979 | Via |
| 4,144,156 A | 3/1979 | Kuesters et al. |
| 4,148,658 A | 4/1979 | Kondoh et al. |
| 4,162,162 A | 7/1979 | Dueber |
| 4,171,977 A | 10/1979 | Hasegawa et al. |
| 4,179,577 A | 12/1979 | Green |
| 4,181,807 A | 1/1980 | Green |
| 4,190,671 A | 2/1980 | Vanstone et al. |
| 4,197,080 A | 4/1980 | Mee |
| 4,199,420 A | 4/1980 | Photis |
| 4,229,172 A | 10/1980 | Baumann et al. |
| 4,232,106 A | 11/1980 | Iwasaki et al. |
| 4,238,492 A | 12/1980 | Majoie |
| 4,239,843 A | 12/1980 | Hara et al. |
| 4,239,850 A | 12/1980 | Kita et al. |
| 4,241,155 A | 12/1980 | Hara et al. |
| 4,242,430 A | 12/1980 | Hara et al. |
| 4,242,431 A | 12/1980 | Hara et al. |
| 4,245,018 A | 1/1981 | Hara et al. |
| 4,245,033 A | 1/1981 | Eida et al. |
| 4,245,995 A | 1/1981 | Hugl et al. |
| 4,246,330 A | 1/1981 | Hara et al. |
| 4,248,949 A | 2/1981 | Hara et al. |
| 4,250,096 A | 2/1981 | Kvita et al. |
| 4,251,622 A | 2/1981 | Kimoto et al. |
| 4,251,662 A | 2/1981 | Ozawa et al. |
| 4,254,195 A | 3/1981 | Hara et al. |
| 4,256,493 A | 3/1981 | Yokoyama et al. |
| 4,256,817 A | 3/1981 | Hara et al. |
| 4,258,123 A | 3/1981 | Nagashima et al. |
| 4,258,367 A | 3/1981 | Mansukhani |
| 4,259,432 A | 3/1981 | Kondoh et al. |
| 4,262,936 A | 4/1981 | Miyamoto |
| 4,268,605 A | 5/1981 | Hara et al. |
| 4,268,667 A | 5/1981 | Anderson |
| 4,269,926 A | 5/1981 | Hara et al. |
| 4,270,130 A | 5/1981 | Houle et al. |
| 4,271,252 A | 6/1981 | Hara et al. |
| 4,271,253 A | 6/1981 | Hara et al. |
| 4,272,244 A | 6/1981 | Schlick |
| 4,276,211 A | 6/1981 | Singer et al. |
| 4,277,497 A | 7/1981 | Fromantin |
| 4,279,653 A | 7/1981 | Makishima et al. |
| 4,279,982 A | 7/1981 | Iwasaki et al. |
| 4,279,985 A | 7/1981 | Nonogaki et al. |
| 4,284,485 A | 8/1981 | Berner |
| 4,288,631 A | 9/1981 | Ching |
| 4,289,844 A | 9/1981 | Specht et al. |
| 4,290,870 A | 9/1981 | Kondoh et al. |
| 4,293,458 A | 10/1981 | Gruenberger et al. |
| 4,298,679 A | 11/1981 | Shinozaki et al. |
| 4,300,123 A | 11/1981 | McMillin et al. |
| 4,301,223 A | 11/1981 | Nakamura et al. |
| 4,302,606 A | 11/1981 | Barabas et al. |
| 4,306,014 A | 12/1981 | Kunikane et al. |
| 4,307,182 A | 12/1981 | Dalzell et al. |
| 4,308,400 A | 12/1981 | Felder et al. |
| 4,315,807 A | 2/1982 | Felder et al. |
| 4,318,705 A | 3/1982 | Nowak et al. |
| 4,318,791 A | 3/1982 | Felder et al. |
| 4,321,118 A | 3/1982 | Felder et al. |
| 4,335,054 A | 6/1982 | Blaser et al. |
| 4,335,055 A | 6/1982 | Blaser et al. |
| 4,336,323 A | 6/1982 | Winslow |
| 4,343,891 A | 8/1982 | Aasen et al. |
| 4,345,011 A | 8/1982 | Drexhage |
| 4,347,111 A | 8/1982 | Gehlhaus et al. |
| 4,349,617 A | 9/1982 | Kawashiri et al. |
| 4,350,753 A | 9/1982 | Shelnut et al. |
| 4,351,893 A | 9/1982 | Anderson |
| 4,356,247 A | 10/1982 | Aotani et al. |
| 4,356,255 A | 10/1982 | Tachikawa et al. |
| 4,357,468 A | 11/1982 | Szejtli et al. |
| 4,359,524 A | 11/1982 | Masuda et al. |
| 4,362,806 A | 12/1982 | Whitmore |
| 4,367,072 A | 1/1983 | Vogtle et al. |
| 4,367,280 A | 1/1983 | Kondo et al. |
| 4,369,283 A | 1/1983 | Altschuler |
| 4,370,401 A | 1/1983 | Winslow et al. |
| 4,372,582 A | 2/1983 | Geisler |
| 4,373,017 A | 2/1983 | Masukawa et al. |
| 4,373,020 A | 2/1983 | Winslow |
| 4,374,984 A | 2/1983 | Eichler et al. |
| 4,376,887 A | 3/1983 | Greenaway et al. |
| 4,383,835 A | 5/1983 | Preuss et al. |
| 4,390,616 A | 6/1983 | Sato et al. |
| 4,391,867 A | 7/1983 | Derick et al. |
| 4,399,209 A | 8/1983 | Sanders et al. |
| 4,400,173 A | 8/1983 | Beavan |
| 4,401,470 A | 8/1983 | Bridger |
| 4,416,961 A | 11/1983 | Drexhage |
| 4,421,559 A | 12/1983 | Owatari |
| 4,424,325 A | 1/1984 | Tsunoda et al. |
| 4,425,162 A | 1/1984 | Sugiyama |
| 4,425,424 A | 1/1984 | Altland et al. |
| 4,426,153 A | 1/1984 | Libby et al. |
| 4,434,035 A | 2/1984 | Eichler et al. |
| 4,440,827 A | 4/1984 | Miyamoto et al. |
| 4,447,521 A | 5/1984 | Tiers et al. |
| 4,450,227 A | 5/1984 | Holmes et al. |
| 4,460,676 A | 7/1984 | Fabel |
| 4,467,112 A | 8/1984 | Matsuura et al. |
| 4,475,999 A | 10/1984 | Via |
| 4,477,681 A | 10/1984 | Gehlhaus et al. |
| 4,489,334 A | 12/1984 | Owatari |
| 4,495,041 A | 1/1985 | Goldstein |
| 4,496,447 A | 1/1985 | Eichler et al. |
| 4,500,355 A | 2/1985 | Shimada et al. |
| 4,508,570 A | 4/1985 | Fugii et al. |
| 4,510,392 A | 4/1985 | Litt et al. |
| 4,523,924 A | 6/1985 | Lacroix |
| 4,524,122 A | 6/1985 | Weber et al. |
| 4,534,838 A | 8/1985 | Lin et al. |
| 4,548,896 A | 10/1985 | Sabongi et al. |
| 4,555,474 A | 11/1985 | Kawamura |
| 4,557,730 A | 12/1985 | Bennett et al. |
| 4,559,371 A | 12/1985 | Hüsler et al. |
| 4,564,560 A | 1/1986 | Tani et al. |
| 4,565,769 A | 1/1986 | Dueber et al. |
| 4,567,171 A | 1/1986 | Mangum |
| 4,571,377 A | 2/1986 | McGinniss et al. |

| | | | | | |
|---|---|---|---|---|---|
| 4,582,862 A | 4/1986 | Berner et al. | 4,853,398 A | 8/1989 | Carr et al. |
| 4,595,745 A | 6/1986 | Nakano et al. | 4,854,971 A | 8/1989 | Gane et al. |
| 4,604,344 A | 8/1986 | Irving et al. | 4,857,438 A | 8/1989 | Loerzer et al. |
| 4,605,442 A | 8/1986 | Kawashita et al. | 4,861,916 A | 8/1989 | Kohler et al. |
| 4,613,334 A | 9/1986 | Thomas et al. | 4,864,324 A | 9/1989 | Shirota et al. ............ 106/31.49 |
| 4,614,723 A | 9/1986 | Schmidt et al. | 4,865,942 A | 9/1989 | Gottschalk et al. |
| 4,617,380 A | 10/1986 | Hinson et al. | 4,874,391 A | 10/1989 | Reinert |
| 4,620,875 A | 11/1986 | Shimada et al. | 4,874,899 A | 10/1989 | Hoelderich et al. |
| 4,620,876 A | 11/1986 | Fugii et al. | 4,885,395 A | 12/1989 | Hoelderich |
| 4,622,286 A | 11/1986 | Sheets | 4,886,774 A | 12/1989 | Doi |
| 4,631,085 A | 12/1986 | Kawanishi et al. | 4,892,941 A | 1/1990 | Dolphin et al. |
| 4,632,891 A | 12/1986 | Banks et al. | 4,895,880 A | 1/1990 | Gottschalk |
| 4,632,895 A | 12/1986 | Patel et al. | 4,900,581 A | 2/1990 | Stuke et al. |
| 4,634,644 A | 1/1987 | Irving et al. | 4,902,299 A | 2/1990 | Anton |
| 4,638,340 A | 1/1987 | Iiyama et al. | 4,902,725 A | 2/1990 | Moore |
| 4,647,310 A | 3/1987 | Shimada et al. | 4,902,787 A | 2/1990 | Freeman |
| 4,655,783 A | 4/1987 | Reinert et al. | 4,911,732 A | 3/1990 | Neumann et al. |
| 4,663,275 A | 5/1987 | West et al. | 4,911,899 A | 3/1990 | Hagiwara et al. |
| 4,663,641 A | 5/1987 | Iiyama et al. | 4,917,956 A | 4/1990 | Rohrbach |
| 4,668,533 A | 5/1987 | Miller | 4,921,317 A | 5/1990 | Suzuki et al. |
| 4,672,041 A | 6/1987 | Jain | 4,925,770 A | 5/1990 | Ichiura et al. |
| 4,698,291 A | 10/1987 | Koibuchi et al. | 4,925,777 A | 5/1990 | Inoue et al. |
| 4,701,402 A | 10/1987 | Patel et al. | 4,926,190 A | 5/1990 | Lavar |
| 4,702,996 A | 10/1987 | Griffing et al. | 4,933,265 A | 6/1990 | Inoue et al. |
| 4,704,133 A | 11/1987 | Reinert et al. | 4,933,948 A | 6/1990 | Herkstroeter |
| 4,707,161 A | 11/1987 | Thomas et al. | 4,937,161 A | 6/1990 | Kita et al. |
| 4,707,425 A | 11/1987 | Sasagawa et al. | 4,942,113 A | 7/1990 | Trundle |
| 4,707,430 A | 11/1987 | Ozawa et al. | 4,944,988 A | 7/1990 | Yasuda et al. |
| 4,711,668 A | 12/1987 | Shimada et al. | 4,950,304 A | 8/1990 | Reinert et al. |
| 4,711,802 A | 12/1987 | Tannenbaum | 4,952,478 A | 8/1990 | Miyagawa et al. |
| 4,713,113 A | 12/1987 | Shimada et al. | 4,952,680 A | 8/1990 | Schmeidl |
| 4,720,450 A | 1/1988 | Ellis | 4,954,380 A | 9/1990 | Kanome et al. |
| 4,721,531 A | 1/1988 | Wildeman et al. | 4,954,416 A | 9/1990 | Wright et al. |
| 4,721,734 A | 1/1988 | Gehlhaus et al. | 4,956,254 A | 9/1990 | Washizu et al. |
| 4,724,021 A | 2/1988 | Martin et al. | 4,964,871 A | 10/1990 | Reinert et al. |
| 4,724,201 A | 2/1988 | Okazaki et al. | 4,965,294 A | 10/1990 | Ohngemach et al. |
| 4,725,527 A | 2/1988 | Robillard | 4,966,607 A | 10/1990 | Shinoki et al. |
| 4,727,824 A | 3/1988 | Ducharme et al. | 4,966,833 A | 10/1990 | Inoue |
| 4,732,615 A | 3/1988 | Kawashita et al. | 4,968,596 A | 11/1990 | Inoue et al. |
| 4,737,190 A | 4/1988 | Shimada et al. | 4,968,813 A | 11/1990 | Rule et al. |
| 4,737,438 A | 4/1988 | Ito et al. | 4,985,345 A | 1/1991 | Hayakawa et al. |
| 4,740,451 A | 4/1988 | Kohara | 4,987,056 A | 1/1991 | Imahashi et al. |
| 4,745,042 A | 5/1988 | Sasago et al. | 4,988,561 A | 1/1991 | Wason |
| 4,746,735 A | 5/1988 | Kruper, Jr. et al. | 4,997,745 A | 3/1991 | Kawamura et al. |
| 4,752,341 A | 6/1988 | Rock | 5,001,330 A | 3/1991 | Koch |
| 4,755,450 A | 7/1988 | Sanders et al. | 5,002,853 A | 3/1991 | Aoai et al. |
| 4,761,181 A | 8/1988 | Suzuki | 5,002,993 A | 3/1991 | West et al. |
| 4,766,050 A | 8/1988 | Jerry | 5,003,142 A | 3/1991 | Fuller |
| 4,766,055 A | 8/1988 | Kawabata et al. | 5,006,758 A | 4/1991 | Gellert et al. |
| 4,770,667 A | 9/1988 | Evans et al. | 5,013,959 A | 5/1991 | Kogelschatz |
| 4,772,291 A | 9/1988 | Shibanai et al. | 5,017,195 A | 5/1991 | Satou et al. |
| 4,772,541 A | 9/1988 | Gottschalk | 5,023,129 A | 6/1991 | Morganti et al. |
| 4,775,386 A | 10/1988 | Reinert et al. | 5,025,036 A | 6/1991 | Carson et al. |
| 4,786,586 A | 11/1988 | Lee et al. | 5,026,425 A | 6/1991 | Hindagolla et al. |
| 4,789,382 A | 12/1988 | Neumann et al. | 5,026,427 A | 6/1991 | Mitchell et al. |
| 4,790,565 A | 12/1988 | Steed | 5,028,262 A | 7/1991 | Barlow, Jr. et al. |
| 4,800,149 A | 1/1989 | Gottschalk | 5,028,792 A | 7/1991 | Mullis |
| 4,803,008 A | 2/1989 | Ciolino et al. | 5,030,243 A | 7/1991 | Reinert |
| 4,808,189 A | 2/1989 | Oishi et al. | 5,030,248 A | 7/1991 | Meszaros |
| 4,812,139 A | 3/1989 | Brodmann | 5,034,526 A | 7/1991 | Bonham et al. |
| 4,812,517 A | 3/1989 | West | 5,037,726 A | 8/1991 | Kojima et al. |
| 4,813,970 A | 3/1989 | Kirjanov et al. | 5,045,435 A | 9/1991 | Adams et al. |
| 4,822,714 A | 4/1989 | Sanders | 5,045,573 A | 9/1991 | Kohler et al. |
| 4,831,068 A | 5/1989 | Reinert et al. | 5,047,556 A | 9/1991 | Kohler et al. |
| 4,834,771 A | 5/1989 | Yamauchi et al. | 5,049,777 A | 9/1991 | Mechtersheimer |
| 4,837,106 A | 6/1989 | Ishikawa et al. | 5,053,320 A | 10/1991 | Robillard |
| 4,837,331 A | 6/1989 | Yamanishi et al. | 5,055,579 A | 10/1991 | Pawlowski et al. |
| 4,838,938 A | 6/1989 | Tomida et al. | 5,057,562 A | 10/1991 | Reinert |
| 4,839,269 A | 6/1989 | Okazaki et al. | 5,068,140 A | 11/1991 | Malhotra et al. |
| 4,849,320 A | 7/1989 | Irving et al. | 5,068,364 A | 11/1991 | Takagaki et al. |
| 4,853,037 A | 8/1989 | Johnson et al. | 5,069,681 A | 12/1991 | Bouwknegt et al. |

| Patent | Date | Inventor |
|---|---|---|
| 5,070,001 A | 12/1991 | Stahlhofen |
| 5,073,448 A | 12/1991 | Vieira et al. |
| 5,074,885 A | 12/1991 | Reinert |
| 5,076,808 A | 12/1991 | Hahn et al. |
| 5,077,402 A | 12/1991 | Desobry et al. |
| 5,085,698 A | 2/1992 | Ma et al. |
| 5,087,550 A | 2/1992 | Blum et al. |
| 5,089,050 A | 2/1992 | Vieira et al. |
| 5,089,374 A | 2/1992 | Saeva |
| 5,096,456 A | 3/1992 | Reinert et al. |
| 5,096,489 A | 3/1992 | Laver |
| 5,096,781 A | 3/1992 | Vieira et al. |
| 5,098,477 A | 3/1992 | Vieira et al. |
| 5,098,793 A | 3/1992 | Rohrbach et al. |
| 5,098,806 A | 3/1992 | Robillard |
| 5,106,723 A | 4/1992 | West et al. |
| 5,108,505 A | 4/1992 | Moffat |
| 5,108,874 A | 4/1992 | Griffing et al. |
| 5,110,706 A | 5/1992 | Yumoto et al. |
| 5,110,709 A | 5/1992 | Aoai et al. |
| 5,114,832 A | 5/1992 | Zertani et al. |
| 5,124,723 A | 6/1992 | Laver |
| 5,130,227 A | 7/1992 | Wade et al. |
| 5,133,803 A | 7/1992 | Moffatt |
| 5,135,940 A | 8/1992 | Belander et al. |
| 5,139,572 A | 8/1992 | Kawashima |
| 5,139,687 A | 8/1992 | Borgher, Sr. et al. |
| 5,141,556 A | 8/1992 | Matrick |
| 5,141,797 A | 8/1992 | Wheeler |
| 5,144,964 A | 9/1992 | Demian |
| 5,147,901 A | 9/1992 | Rutsch et al. |
| 5,153,104 A | 10/1992 | Rossman et al. |
| 5,153,105 A | 10/1992 | Sher et al. |
| 5,153,166 A | 10/1992 | Jain et al. |
| 5,160,346 A | 11/1992 | Fuso et al. |
| 5,160,372 A | 11/1992 | Matrick |
| 5,166,041 A | 11/1992 | Murofushi et al. |
| 5,169,436 A | 12/1992 | Matrick |
| 5,169,438 A | 12/1992 | Matrick |
| 5,173,112 A | 12/1992 | Matrick et al. |
| 5,176,984 A | 1/1993 | Hipps, Sr. et al. |
| 5,178,420 A | 1/1993 | Shelby |
| 5,180,425 A | 1/1993 | Matrick et al. |
| 5,180,624 A | 1/1993 | Kojima et al. |
| 5,180,652 A | 1/1993 | Yamaguchi et al. |
| 5,181,935 A | 1/1993 | Reinert et al. |
| 5,185,236 A | 2/1993 | Shiba et al. |
| 5,187,045 A | 2/1993 | Bonham et al. |
| 5,187,049 A | 2/1993 | Sher et al. |
| 5,190,565 A | 3/1993 | Berenbaum et al. |
| 5,190,710 A | 3/1993 | Kletecka |
| 5,190,845 A | 3/1993 | Hashimoto et al. |
| 5,193,854 A | 3/1993 | Borowski, Jr. et al. |
| 5,196,295 A | 3/1993 | Davis |
| 5,197,991 A | 3/1993 | Rembold |
| 5,198,330 A | 3/1993 | Martic et al. |
| 5,202,209 A | 4/1993 | Winnik et al. |
| 5,202,210 A | 4/1993 | Matsuoka et al. |
| 5,202,211 A | 4/1993 | Vercoulen |
| 5,202,212 A | 4/1993 | Shin et al. |
| 5,202,213 A | 4/1993 | Nakahara et al. |
| 5,202,215 A | 4/1993 | Kanakura et al. |
| 5,202,221 A | 4/1993 | Imai et al. |
| 5,205,861 A | 4/1993 | Matrick |
| 5,208,136 A | 5/1993 | Zanoni et al. |
| 5,209,814 A | 5/1993 | Felten et al. |
| 5,219,703 A | 6/1993 | Bugner et al. |
| 5,221,334 A | 6/1993 | Ma et al. |
| 5,224,197 A | 6/1993 | Zanoni et al. |
| 5,224,987 A | 7/1993 | Matrick |
| 5,226,957 A | 7/1993 | Wickramanayake et al. |
| 5,227,022 A | 7/1993 | Leonhardt et al. |
| 5,230,982 A | 7/1993 | Davis et al. |
| 5,241,059 A | 8/1993 | Yoshinaga |
| 5,244,476 A | 9/1993 | Schulz et al. |
| 5,250,109 A | 10/1993 | Chan et al. |
| 5,254,429 A | 10/1993 | Gracia et al. |
| 5,256,193 A | 10/1993 | Winnik et al. |
| 5,258,274 A | 11/1993 | Helland et al. |
| 5,261,953 A | 11/1993 | Vieira et al. |
| 5,262,276 A | 11/1993 | Kawamura |
| 5,268,027 A | 12/1993 | Chan et al. |
| 5,270,078 A | 12/1993 | Walker et al. |
| 5,271,764 A | 12/1993 | Winnik et al. |
| 5,271,765 A | 12/1993 | Ma |
| 5,272,201 A | 12/1993 | Ma et al. |
| 5,275,646 A | 1/1994 | Marshall et al. |
| 5,279,652 A | 1/1994 | Kaufmann et al. |
| 5,282,894 A | 2/1994 | Albert et al. |
| 5,284,734 A | 2/1994 | Blum et al. |
| 5,286,286 A | 2/1994 | Winnik et al. |
| 5,286,288 A | 2/1994 | Tobias et al. |
| 5,294,528 A | 3/1994 | Furutachi |
| 5,296,275 A | 3/1994 | Goman et al. |
| 5,296,556 A | 3/1994 | Frihart |
| 5,298,030 A | 3/1994 | Burdeska et al. |
| 5,300,403 A | 4/1994 | Angelopolus et al. |
| 5,300,654 A | 4/1994 | Nakajima et al. |
| 5,302,195 A | 4/1994 | Helbrecht |
| 5,302,197 A | 4/1994 | Wickramanayke et al. |
| 5,310,778 A | 5/1994 | Shor et al. |
| 5,312,713 A | 5/1994 | Yokoyama et al. |
| 5,312,721 A | 5/1994 | Gesign |
| 5,324,349 A | 6/1994 | Sano et al. |
| 5,328,504 A | 7/1994 | Ohnishi |
| 5,330,860 A | 7/1994 | Grot et al. |
| 5,334,455 A | 8/1994 | Noren et al. |
| 5,338,319 A | 8/1994 | Kaschig et al. |
| 5,340,631 A | 8/1994 | Matsuzawa et al. |
| 5,340,854 A | 8/1994 | Martic et al. |
| 5,344,483 A | 9/1994 | Hinton |
| 5,356,464 A | 10/1994 | Hickman et al. |
| 5,362,592 A | 11/1994 | Murofushi et al. |
| 5,362,916 A | 11/1994 | Edwards et al. |
| 5,368,689 A | 11/1994 | Agnemo |
| 5,372,387 A | 12/1994 | Wajda |
| 5,372,917 A | 12/1994 | Tsuchida et al. |
| 5,374,335 A | 12/1994 | Lindgren et al. |
| 5,376,503 A | 12/1994 | Audett et al. |
| 5,383,961 A | 1/1995 | Bauer et al. |
| 5,384,186 A | 1/1995 | Trinh |
| 5,393,580 A | 2/1995 | Ma et al. |
| 5,401,303 A | 3/1995 | Stoffel et al. |
| 5,401,562 A | 3/1995 | Akao |
| 5,407,969 A | 4/1995 | Kleiner et al. |
| 5,415,686 A | 5/1995 | Kurabayashi et al. |
| 5,415,976 A | 5/1995 | Ali |
| 5,424,407 A | 6/1995 | Tanaka et al. |
| 5,425,978 A | 6/1995 | Berneth et al. |
| 5,426,164 A | 6/1995 | Babb et al. |
| 5,427,415 A | 6/1995 | Chang |
| 5,429,628 A | 7/1995 | Trinh et al. |
| 5,431,720 A | 7/1995 | Nagai et al. |
| 5,432,274 A | 7/1995 | Luong et al. |
| 5,445,651 A | 8/1995 | Thoen et al. |
| 5,445,842 A | 8/1995 | Tanaka et al. |
| 5,455,074 A | 10/1995 | Nohr et al. |
| 5,455,143 A | 10/1995 | Ali |
| 5,459,014 A | 10/1995 | Nishijima et al. |
| 5,464,472 A | 11/1995 | Horn et al. |
| 5,466,283 A | 11/1995 | Kondo et al. |
| 5,474,691 A | 12/1995 | Severns |

| | | | | | |
|---|---|---|---|---|---|
| 5,475,080 A | 12/1995 | Gruber et al. | CA | 517364 | 10/1955 |
| 5,476,540 A | 12/1995 | Shields et al. | CA | 537687 | 3/1957 |
| 5,479,949 A | 1/1996 | Battard et al. | CA | 552565 | 2/1958 |
| 5,489,503 A | 2/1996 | Toan | CA | 571792 | 3/1959 |
| 5,498,345 A | 3/1996 | Jollenbeck et al. | CA | 779239 | 2/1968 |
| 5,501,774 A | 3/1996 | Burke | CA | 930103 | 7/1973 |
| 5,501,902 A | 3/1996 | Kronzer | CA | 2053094 | 4/1992 |
| 5,503,664 A | 4/1996 | Sano et al. | CH | 603767 | 8/1978 |
| 5,509,957 A | 4/1996 | Toan et al. | CH | 197808 | 5/1988 |
| 5,531,821 A | 7/1996 | Wu | CZ | 94118 | 5/1958 |
| 5,532,112 A | 7/1996 | Kohler et al. | DE | 1047787 | 12/1957 |
| 5,541,633 A | 7/1996 | Winnik et al. | DE | 1022801 | 1/1958 |
| 5,543,459 A | 8/1996 | Hartmann et al. | DE | 1039835 | 9/1958 |
| 5,569,529 A | 10/1996 | Becker et al. | DE | 1040562 | 10/1958 |
| 5,571,313 A | 11/1996 | Mafune et al. | DE | 1045414 | 12/1958 |
| 5,575,891 A | 11/1996 | Trokhan et al. | DE | 1047013 | 12/1958 |
| 5,580,369 A | 12/1996 | Belding et al. | DE | 1132540 | 7/1962 |
| 5,591,489 A | 1/1997 | Dragner et al. | DE | 1154069 | 9/1963 |
| 5,597,405 A | 1/1997 | Grigoryan et al. | DE | 1240811 | 5/1967 |
| 5,607,803 A | 3/1997 | Murofushi et al. | DE | 2202497 | 8/1972 |
| 5,616,443 A | 4/1997 | Nohr et al. | DE | 2432563 | 2/1975 |
| 5,635,297 A | 6/1997 | Ogawa et al. | DE | 2437380 | 2/1975 |
| 5,643,356 A | 7/1997 | Nohr et al. | DE | 2444520 | 3/1975 |
| 5,643,631 A | 7/1997 | Donigian et al. | DE | 2416259 | 10/1975 |
| 5,643,701 A | 7/1997 | Nohr et al. | DE | 2714978 | 10/1977 |
| 5,645,964 A | 7/1997 | Nohr et al. | DE | 2722264 | 11/1978 |
| 5,672,392 A | 9/1997 | De Clercq et al. | DE | 158237 | 1/1983 |
| 5,681,380 A | 10/1997 | Nohr et al. | DE | 3126433 | 1/1983 |
| 5,683,843 A | 11/1997 | Nohr et al. | DE | 3415033 | 10/1984 |
| 5,685,754 A | 11/1997 | Nohr et al. | DE | 271512 | 9/1989 |
| 5,686,503 A | 11/1997 | Nohr et al. | DE | 3921600 | 1/1990 |
| 5,700,582 A | 12/1997 | Sargeant et al. | DE | 3833437 | 4/1990 |
| 5,700,850 A | 12/1997 | Nohr et al. | DE | 3833438 | 4/1990 |
| 5,705,247 A | 1/1998 | Arai et al. | DE | 004036328 | 7/1991 |
| 5,709,955 A | 1/1998 | Nohr et al. | DE | 4132288 | 4/1992 |
| 5,709,976 A | 1/1998 | Malhotra | DE | 4126461 | 2/1993 |
| 5,721,287 A | 2/1998 | Nohr et al. | EP | 0003884 | 9/1979 |
| 5,733,693 A | 3/1998 | Nohr et al. | EP | 0029284 | 5/1981 |
| 5,738,716 A | 4/1998 | Santilli et al. ............ 106/31.77 | EP | 0127574 | 12/1984 |
| 5,738,932 A | 4/1998 | Kondo et al. | EP | 0202803 | 11/1986 |
| 5,739,175 A | 4/1998 | Nohr et al. | EP | 0 209 831 | 1/1987 |
| 5,747,550 A | 5/1998 | Nohr et al. | EP | 0223587 | 5/1987 |
| 5,773,182 A | 6/1998 | Nohr et al. | EP | 0262533 | 4/1988 |
| 5,782,963 A | 7/1998 | Nohr et al. | EP | 0280458 | 8/1988 |
| 5,786,132 A | 7/1998 | Nohr et al. | EP | 0 303 803 | 2/1989 |
| 5,798,015 A | 8/1998 | Nohr et al. | EP | 0308274 | 3/1989 |
| 5,811,199 A | 9/1998 | MacDonald et al. | EP | 0351615 | 1/1990 |
| 5,837,429 A | 11/1998 | Nohr et al. | EP | 0371304 | 6/1990 |
| 5,849,411 A | 12/1998 | Nohr et al. | EP | 0373662 | 6/1990 |
| 5,855,655 A | 1/1999 | Nohr et al. | EP | 0375160 | 6/1990 |
| 5,856,515 A | 1/1999 | Therien et al. | EP | 0390439 | 10/1990 |
| 5,864,044 A | 1/1999 | Van Lier et al. ............ 548/405 | EP | 0433201 | 6/1991 |
| 5,865,471 A | 2/1999 | Nohr et al. | EP | 0458140 A1 | 10/1991 |
| 5,883,161 A | 3/1999 | Wood et al. | EP | 0458140 | 11/1991 |
| 5,885,337 A | 3/1999 | Nohr et al. | EP | 0468465 | 1/1992 |
| 5,891,229 A | 4/1999 | Nohr et al. | EP | 0 469 595 | 2/1992 |
| 5,911,855 A | 6/1999 | Dransmann et al. | EP | 0 475 075 | 3/1992 |
| 6,022,906 A | 2/2000 | Ohwa et al. | EP | 0542286 | 5/1993 |
| | | | EP | 000571190 | 11/1993 |
| | FOREIGN PATENT DOCUMENTS | | EP | 0 605 840 | 7/1994 |
| BE | 637169 | 3/1964 | EP | 0608433 | 8/1994 |
| CA | 413257 | 10/1932 | EP | 0609159 | 8/1994 |
| CA | 458808 | 12/1936 | EP | 0 635 380 | 1/1995 |
| CA | 460268 | 10/1949 | EP | 0639664 | 2/1995 |
| CA | 461082 | 11/1949 | EP | 0658607 | 6/1995 |
| CA | 463021 | 2/1950 | EP | 0 673 779 | 9/1995 |
| CA | 463022 | 2/1950 | EP | 0694594 | 1/1996 |
| CA | 465495 | 5/1950 | EP | 0 716 929 | 6/1996 |
| CA | 465496 | 5/1950 | EP | 0 737 592 | 10/1996 |
| CA | 465499 | 5/1950 | EP | 0755984 | 1/1997 |
| CA | 483214 | 5/1952 | EP | 0 805 152 | 11/1997 |

| | | | | | | |
|---|---|---|---|---|---|---|
| EP | 0 861 880 | 9/1998 | | JP | 63-48370 | 3/1988 |
| EP | 0864620 A1 | 9/1998 | | JP | 6395439 | 4/1988 |
| EP | 0878482 | 11/1998 | | JP | 6395440 | 4/1988 |
| FR | 2245010 | 4/1975 | | JP | 6395445 | 4/1988 |
| FR | 2383157 | 10/1978 | | JP | 6395446 | 4/1988 |
| GB | 275245 | 10/1928 | | JP | 6395447 | 4/1988 |
| GB | 349339 | 5/1931 | | JP | 6395448 | 4/1988 |
| GB | 355686 | 8/1931 | | JP | 6395449 | 4/1988 |
| GB | 399753 | 10/1933 | | JP | 6395450 | 4/1988 |
| GB | 441085 | 1/1936 | | JP | 63151946 | 6/1988 |
| GB | 463515 | 4/1937 | | JP | 63-164953 | 7/1988 |
| GB | 492711 | 9/1938 | | JP | 63-165498 | 7/1988 |
| GB | 518612 | 3/1940 | | JP | 63-223077 | 9/1988 |
| GB | 539912 | 9/1941 | | JP | 63-223078 | 9/1988 |
| GB | 626727 | 7/1947 | | JP | 63-243101 | 10/1988 |
| GB | 600451 | 4/1948 | | JP | 63-199781 | 12/1988 |
| GB | 616362 | 1/1949 | | JP | 64-15049 | 1/1989 |
| GB | 618616 | 2/1949 | | JP | 6429337 | 1/1989 |
| GB | 779389 | 7/1957 | | JP | 64-40948 | 2/1989 |
| GB | 1150987 | 5/1969 | | JP | 89014948 | 3/1989 |
| GB | 1372884 | 11/1974 | | JP | 1-128063 | 5/1989 |
| GB | 2146357 | 4/1985 | | JP | 1146974 | 6/1989 |
| IT | 662500 | 4/1965 | | JP | 01210477 | 8/1989 |
| JP | 4315663 | 7/1968 | | JP | 1288854 | 11/1989 |
| JP | 4726653 | 7/1972 | | JP | 2-58573 | 2/1990 |
| JP | 4745409 | 11/1972 | | JP | 292957 | 4/1990 |
| JP | 49-8909 | 2/1974 | | JP | 2179642 | 7/1990 |
| JP | 5065592 | 6/1975 | | JP | 2282261 | 11/1990 |
| JP | 51-17802 | 2/1976 | | JP | 3-134072 | 6/1991 |
| JP | 53-104321 | 9/1978 | | JP | 03163566 | 7/1991 |
| JP | 55-62059 | 5/1980 | | JP | 3-170415 | 7/1991 |
| JP | 55-90506 | 7/1980 | | JP | 3-206439 | 9/1991 |
| JP | 56-8134 | 1/1981 | | JP | 3-258867 | 11/1991 |
| JP | 0014233 | 2/1981 | | JP | 3-203694 | 12/1991 |
| JP | 5614569 | 2/1981 | | JP | 3284668 | 12/1991 |
| JP | 56-24472 | 3/1981 | | JP | 4023884 | 1/1992 |
| JP | 56-36556 | 4/1981 | | JP | 4023885 | 1/1992 |
| JP | 5761055 | 4/1982 | | JP | 4-45174 | 2/1992 |
| JP | 57128283 | 8/1982 | | JP | 4100801 | 4/1992 |
| JP | 57171775 | 10/1982 | | JP | 4-136075 | 5/1992 |
| JP | 58-124452 | 7/1983 | | JP | 04356087 | 12/1992 |
| JP | 58-125770 | 7/1983 | | JP | 543806 | 2/1993 |
| JP | 58-222164 | 12/1983 | | JP | 561220 | 3/1993 |
| JP | 5989360 | 5/1984 | | JP | 5080506 | 4/1993 |
| JP | 29219270 | 12/1984 | | JP | 05119506 | 5/1993 |
| JP | 59-219270 | 4/1985 | | JP | 5134447 | 5/1993 |
| JP | 60-192729 | 10/1985 | | JP | 5-140498 | 6/1993 |
| JP | 60239739 | 11/1985 | | JP | 2-219869 | 9/1993 |
| JP | 60239740 | 11/1985 | | JP | 5263067 | 10/1993 |
| JP | 60239741 | 11/1985 | | JP | 680915 | 3/1994 |
| JP | 60239743 | 11/1985 | | JP | 6116555 | 4/1994 |
| JP | 61-288 | 1/1986 | | JP | 6116556 | 4/1994 |
| JP | 613781 | 1/1986 | | JP | 6116557 | 4/1994 |
| JP | 61-14994 | 1/1986 | | JP | 6-175584 | 6/1994 |
| JP | 61-14995 | 1/1986 | | JP | 6214339 | 8/1994 |
| JP | 61-21184 | 1/1986 | | JP | 6256494 | 9/1994 |
| JP | 61-25885 | 2/1986 | | JP | 6256633 | 9/1994 |
| JP | 61-30592 | 2/1986 | | NL | 7113828 | 4/1972 |
| JP | 61-40366 | 2/1986 | | RU | 1310767 | 5/1987 |
| JP | 61-77846 | 4/1986 | | RU | 1772118 | 10/1992 |
| JP | 61-128973 | 6/1986 | | WO | 92/11295 | 7/1992 |
| JP | 61-97025 | 9/1986 | | WO | 93/06597 | 4/1993 |
| JP | 61-222789 | 10/1986 | | WO | 94/01503 | 1/1994 |
| JP | 61-247703 | 11/1986 | | WO | 94/22500 | 10/1994 |
| JP | 61-285403 | 12/1986 | | WO | 94/22501 | 10/1994 |
| JP | 627703 | 1/1987 | | WO | WO 94/24612 | 10/1994 |
| JP | 62-97881 | 5/1987 | | WO | 95/04955 | 2/1995 |
| JP | 62-100557 | 5/1987 | | WO | 95/28285 | 10/1995 |
| JP | 62127281 | 6/1987 | | WO | 96/00740 | 1/1996 |
| JP | 424756 | 1/1988 | | WO | 96/19502 | 6/1996 |
| JP | 63-43959 | 2/1988 | | WO | 96/22335 | 7/1996 |

| | | |
|---|---|---|
| WO | 96/24636 | 8/1996 |
| WO | 97/20000 | 6/1997 |
| WO | 97/35933 | 10/1997 |
| WO | 98/23695 | 6/1998 |
| WO | 99/36476 | 7/1999 |

OTHER PUBLICATIONS

Derwent World Patents Index, Jp 3009939B2 (Ricoh KK), Feb. 14, 2000, abstract.
Patent Abstracts of Japan, JP 07102251 (Toyo Ink Mfg Co Ltd), Apr. 18, 1995, abstract.
Noguchi, H. UV Curable, Aqueous Ink Jet Ink: Material Design and Performance for Digital Printing 1998 International Conf. on Digital Printing Technologies 107–110 1998, no month available.
ESP@CENET database JP 10324836 (Omron Corp.), Dec. 8, 1998. abstract.
Wang et al. Effects of substituenta attached at benzaldehyde on the synthesis and properties of porphyrins *Chem Abstracts* 113(9) 1996, no month available.
Derwent World Patents Index JP 8002092 (Mitsubishi Paper Mills Ltd.) Jan. 9, 1996. abstract.
Kubat et al. "Photophysical properties of metal complexes of meso–tetrakis (40sulphonatophenyl) porphyrin," *J. Photochem. and Photobiol.* 96 93–97 1996, no month available.
Derwent World Patents Index EP 659039 (Canon KK) Jun. 21, 1995. abstract.
Derwent World Patents Index JP 7061114 (Dainippon Printing Co. Ltd.) Mar. 7, 1995. abstract.
Abstract for WO 95/00343—A1 *Textiles: Paper: Cellulose* p. 7 1995, no month available.
Maki, Y. et al. "A novel heterocyclic N–oxide, pyrimido[5,4–g]pteridinetetrone 5–oxide, with multifunctional photooxidative properties" *Chemical Abstracts* 122 925 [No. 122:31350F] 1995, no month available.
Patent Abstracts of Japan JP 06200204 (Brother Ind Ltd), Jul. 19, 1994.
Abstract of patent, JP 6–80915 (Canon Inc.), Mar. 22, 1994.
Abstract of patent, JP 06–43573 (Iku Meji) (Feb. 18, 1994).
Pitchumani, K. et al. "Modification of chemical reactivity upon cyclodextrin encapsulation" *Chemical Abstracts* 121 982 [No. 121:133624v] 1994, no month available.
Wijesekera, T.P., et al. Synthetic Aspects of Pophyrin and Metalloporphyrin Chemistry *Metalloporpyrins in Catalytic Oxidations* pp. 202–203, 206–207, 1994, no month available.
Derwent Publication Ltd., London, JP 05297627 (Fujitsu Ltd.), Nov. 12, 1993. (Abstract).
Patent Abstracts of Japan, JP 5241369 (Bando Chem Ind Ltd et al.), Sep. 21, 1993. (Abstract).
Derwent Publications Ltd., London, JP 05232738 (Yamazaki, T.), Sep. 10, 1993. (Abstract).
Derwent Publications Ltd., London, EP 000559310 (Zeneca Ltd.), Sep. 8, 1993. (Abstract).
Derwent Publications Ltd., London, J,A, 5–230410 (Seiko Epson Corp), Sep. 7, 1993. (Abstract).
Derwent Publications Ltd., London, JP 5–230407 (Mitsubishi Kasei Corp), Sep. 7, 1993. (Abstract).
Abstract Of Patent, JP 405230410 (Seiko Epson Corp.), Sep. 7, 1993. (Abstract).
Abstract of Patent, JP 405230407 (Mitsubishi Kasei Corp.), Sep. 7, 1993. (Abstract).
Patent Abstracts of Japan, JP 5197198 (Bando Chem Ind Ltd et al.), Aug. 6, 1993. (Abstract).

Database WIP—Derwent Publications Ltd., London, J,A, 5197069 (Bando Chem), Aug. 6, 1993. (Abstract).
Abstract of patent, JP 5–195450 (Nitto Boseki Co. Ltd), Aug. 8, 1993.
Derwent World Patents Index JP 5186725 (Seiko Epson Corp.), Jul. 27, 1993. abstract.
Patent Abstracts of Japan, JP 5181308 (Bando Chem Ind Ltd et al.), Jul. 23, 1993. (Abstract).
Patent Abstracts of Japan, JP 5181310 (Bando Chem Ind Ltd et al.), Jul. 23, 1993. (Abstract).
Derwent Publications Ltd., London, JP 5–132638 (Mitsubishi Kasei Corp), May 28, 1993. (Abstract).
Abstract Of Patent JP 405132638 (Mitsubishi Kasei Corp.), May 28, 1993. (Abstract).
Derwent Publications Ltd., London, JP 5–125318 (Mitsubishi Kasei Corp), May 21, 1993. (Abstract).
Abstract of Patent, JP 405125318 (Mitsubishi Kasei Corp.), May 21, 1993. (Abstract).
Abstract of Patent, JP 05–117200 (Hidefumi Hirai et al.) (May 14, 1993).
Derwent World Patents Index, JP 5117105 (Mitsui Toatsu Chem Inc.) May 14, 1993.
Derwent Publications Ltd., London, JP 05061246 (Ricoh KK), Mar. 12, 1993. (Abstract).
Husain, N. et al. "Cyclodextrins as mobile–phase additives in reversed–phase HPLC" *American Laboratory* 82 80–87 1993, no month available.
Hamilton, D.P. "Tired of Shredding? New Ricoh Method Tries Different Tack" *Wall Street Journal* B2 1993, no month available.
"Cyclodextrins: A Breakthrough for Molecular Encapsulation" *American Maize Products Co. (AMAIZO)* 1993, no month available.
Duxbury "The Photochemistry and Photophysics of Triphenylmethane Dyes in Solid Liquid Media" *Chemical Review* 93 381–433 1993, no month available.
Abstract of patent, JP 04–351603 (Dec. 7, 1992).
Abstract of patent, JP 04–351602 1992, no month available.
Derwent Publications Ltd., London, JP 404314769 (Citzen Watch Co. Ltd.), Nov. 5, 1992. (Abstract).
Abstract of patent, JP 04315739 1992, no month available.
Derwent Publications Ltd., London, JP 04300395 (Funai Denki KK), Oct. 23, 1992. (Abstract).
Derwent Publications Ltd., London, JP 404213374 (Mitsubishi Kasei Corp), Aug. 4, 1992. (Abstract).
Abstract of patent, JP 04–210228 1992, no month available.
Abstract Of Patent, JP 404202571 (Canon Inc.), Jul. 23, 1992. (Abstract).
Abstract Of Patent, JP 404202271 (Mitsubishi Kasei Corp.), Jul. 23, 1992. (Abstract).
Derwent WPI, JP 4–197657 (Toshiba KK) Jul. 17, 1992, abstract.
Derwent Publications Ltd., London, JP 4–189877 (Seiko Epson Corp), Jul. 8, 1992. (Abstract).
Derwent Publications Ltd., London, JP 404189876 (Seiko Epson Corp), Jul. 8, 1992. (Abstract).
Abstract Of Patent, JP 404189877 (Seiko Epson Corp.), Jul. 8, 1992. (Abstract).
Derwent Publications Ltd., London, J,A, 4–170479 (Seiko Epson Corp), Jun. 18, 1992. (Abstract).
Abstract of patent, JP 04–81402 1992, no month available.
Abstract of patent, JP 04–81401 1992, no month available.

Kogelschatz "Silent–discharge driven excimer UV sources and their applications" *Applied Surface Science* 410–423 1992, no month available.

Patent Abstracts of Japan JP 03295653 (Matsushita Electric Works Ltd.), Dec. 26, 1991.

Derwent Publications, Ltd., London, JP 403269167 (Japan Wool Textile KK), Nov. 29, 1991 (Abstract).

Derwent Publications Ltd., London, JO 3247676 (Canon KK), Nov. 5, 1991 (Abstract).

Tang, F. Synthesis and Properties of 5, 10, 15, 20–tetrakis (4–=methoxyl–3–sulfophenyl) porphine *Chem. Abstracts* 115(17) 1991, no month available.

Abstract of patent, JP 03–220384 1991, no month available.

Patent Abstracts of Japan, JP 03184896 (Dainipppon Printing Co Ltd.) Aug. 12, 1991.

Derwent Publications Ltd., London, JP 3167270 (Mitsubishi Kasei Corp), Jul. 19, 1991. (Abstract).

Derwent Publications Ltd., London, JO 3167270 (Mitsubishi Kasei Corp.), Jul. 19, 1991 (Abstract).

Derwent World Patents Index EP 435536 (Canon KK) abstract Jul. 3, 1991.

Derwent Publications Ltd., London, JO 3093870 (Dainippon Ink Chem KK.), Apr. 18, 1991 (Abstract).

Abstract of patent, JP 06369890 1991, no month available.

Kogelschatz, U. et al. "New Excimer UV Sources for Industrial Applications" *ABB Review* 391 1–10 1991, no month available.

Abstract of patent, JP 03–41165 1991, no month available.

"Coloring/Decoloring Agent for Tonor Use Developed" *Japan Chemical Week* , 1991, no month available.

Braithwaite, M., et al. "Formulation" *Chemistry & Technology of UV & EB Formulation for Coatings, Inks & Paints* IV 11–12 1991, no month available.

Scientific Polymer Products, Inc. Brochure 24–31 1991, no month available.

Dietliker, K. "Photoiniators for Free Radical and Cationic Polymerisation" *Chem & Tech of UV & EB Formulation for Coatings, Inks & Paints* III 61, 63, 229–232, 280, 405, 1991, no month available.

Esrom et al. "Large area Photochemical Dry Etching of Polymers iwth Incoherent Excimer UV Radiation" *MRS Materials Research Society* 1–7 1991, no month available.

Esrom et al. Excimer Laser–Induced Decomposition of Aluminum Nitride Materials Research Society Fall Meeting 1–6 1991, no month available.

Esrom et al. "Metal deposition with a windowless VUV excimer source" *Applied Surface Science* 1–5 1991, no month available.

Esrom "Excimer Laser–Induced Surface Activation of Aln for Electroless Metal Deposition" *Mat. Res. Sco.1Symp. Proc.* 204 457–465 1991, no month available.

Zhang et al. "UV–induced decompositin of adsorbed Cu–acetylacetonate films at room temperature for electroless metal plating" *Applied Surface Science* 1–6 1991, no month available.

"German company develops reusable paper" *Pulp & Paper* 1991, no month available.

Abstract of patent, JP 02289652 1990, no month available.

Ohashi et al. "Molecular Mechanics Studies on Inclusion Compounds of Cyanine Dye Monomers and Dimers in Cyclodextrin Cavities," *J. Am. Chem. Soc.* 112 5824–5830 1990, no month available.

Kogelschatz et al. "New Incoherent Ultraviolet Excimer Sources for Photolytic Material Disposition," *Laser Und Optoelektronik* 1990, no month available.

Patent Abstracts of Japan, JP 02141287 (Dainippon Printing Co Ltd.) May 30, 1990.

Abstract of Patent, JP 0297957, (Fuji Xerox Co., Ltd.) 1990.

Derwent Publications Ltd., London, JP 2091166 (Canon KK), Mar. 30, 1990. (Abstract).

Zhang, Zhoupeng Synthesis of 7 meso–tetrasubstituted porphyrins *Chem. Abstracts* 113(9) 1990, no month available.

Esrom et al. "Metal Deposition with Incoherent Excimer Radiation" *Mat. Res. Soc. Symp. Proc.* 158 189–198 1990, no month available.

Esrom "UV Excimer Laser–Induced Deposition of Palladium from palladiym Acetate Films" *Mat. Res. Soc. Symp. Proc.* 158 109–117 1990, no month available.

Kogelschatz, U. "Silent Discharges for the Generation of ultraviolet and vacuum ultraviolet excimer radiation" *Pure & Applied Chem.* 62 1667–74, 1990, no month available.

Esrom et al. "Investigation of the mechanism of the UV–induced palladium depostions processf from thin solid palladium acetate films" *Applied Surface Science* 46 158–162 1990, no month available.

Zhang et al. "VUV synchrotron radiation processing of thin palladium acetate spin–on films for metallic surface patterning" *Canadian J. Chem.* 68(10) pp. 1780–1785 1990, no month available.

Abstract of patent, JP 01–299083 1989, no month available.

Derwent Publications Ltd., London, J,O, 1182379 (Canon KK), Jul. 20, 1989. (Abstract).

Derwent Publications Ltd., London, JO 1011171 (Mitsubishi Chem Ind. KK.), Jan. 13, 1989 (Abstract).

Gruber, R.J., et al. "Xerographic Materials" *Encyclopedia of Polymer Science and Engineering* 17 918–943 1989, no month available.

Pappas, S.P. "Photocrosslinking" *Comph. Pol. Sci.* 6 135–148 1989, no month available.

Pappas, S.P. "Photoinitiated Polymerization" *Comph. Pol. Sci.* 4 337–355 1989, no month available.

Kirilenko, G.V. et al. "An analog of the vesicular process with amplitude modification of the incident light beam" *Chemical Abstracts* 111 569 [No. 111:123633b] 1989, no month available.

Esrom et al. "UV excimer laser–induced pre–nucleation of surfaces followed by electroless metallization" *Chemtronics* 4 216–223 1989, no month available.

Esrom et al. "VUV light–induced depostion of palladium using an incoherent Xe2* excimer source" *Chemtronics* 4 1989, no month available.

Esrom et al. "UV Light–Induced Depostion of Copper Films" C5–719–C5–725 1989, no month available.

Falbe et al. *Rompp Chemie Lexikon* 9 270 1989, no month available.

Allen, Norman S. *Photopolymerisation and Photoimaging Science and Technology* pp. 188–199; 219–239 1989, no month available.

Lindsey, J.S. et al. Investigation of the Synthesis of Ortho-–Substituted Tetraphenylporphyrins *J. Org. Chem.* 54 pp. 828–836 1989, no month available.

Patent Abstracts of Japan, JP 63297477 (Fuji Photo Film Co. Ltd.) Dec. 5, 1988, abstract.

Derwent Publications, Ltd., London, SU 1423656 (Kherson Ind Inst), Sep. 15, 1988 (Abstract).

Derwent Publications, Ltd., London, EP 0280653 (Ciba Geigy AG), Aug. 31, 1988 (Abstract).
Abstract of patent, JP 63–190815 1988, no month available.
Patent Abstracts of Japan, JP 63179985 (Tomoegawa Paper Co. Ltd.), Jul. 23, 1988.
Derwent World Patents Index, JP 63179977 (Tomoegawa Paper Mfg Co Ltd), Jul. 23, 1988.
Furcone, S.Y. et al. "Spin–on B14Sr3Ca3Cu4O16+x superconducting thin films from citrate precursors," *Appl. Phys. Lett.* 52(25) 2180–2182 1988, no month available.
Abstract of patent, JP 63–144329 1988, no month available.
Abstract of patent, JP 63–130164 1988, no month available.
Derwent Publications, Ltd., London, J6 3112770 (Toray Ind. Inc), May 17, 1988 (Abstract).
Derwent Publications, Ltd., London, J6 3108074 (Konishiroku Photo KK), May 12, 1988 (Abstract).
Derwent Publications, Ltd., London, J6 3108073 (Konishiroku Photo KK), May 12, 1988 (Abstract).
Abstract of patent, JP 61–77846 1988, no month available.
Abstract of patent, JP 63–73241 1988, no month available.
Patent Abstracts of Japan JP 63062738 (Seiko Epson Corp), Mar. 19, 1988.
Abstract of patent, JP 63–47762, 1988, no month available.
Abstract of patent, JP 63–47763, 1988, no month available.
Abstract of patent, JP 63–47764, 1988, no month available.
Abstract of patent, JP 63–47765 1988, no month available.
Eliasson, B., et al. "UV Excimer Radiation from Dielectric–Barrier Discharges" *Applied Physics B* 46 299–303 1988, no month available.
Eliasson et al. "New Trends in High Intensity UV Generation" *EPA Newsletter* (32) 29–40 1988, no month available.
Cotton, F.A. "Oxygen: Group Via(16)" *Advanced Inorganic Chemistry* 5th ed. 473–474 1988, no month available.
Derwent Publications Ltd., London, J6 2270665 (Konishiroku Photo KK), Nov. 25, 1987 (Abstract).
Abstract of patent, JP 62–215261 1987, no month available.
Derwent World Patents Index JP 62064874 (Dainichiseika Color & Chem Mfg.), Mar. 23, 1987. abstract.
Database WPI, Derwent Publications Ltd., London, JP 62032082 (Mitsubishi Denki KK), Feb. 12, 1987. (Abstract).
Abstract of patent, JP 62–32082 1987, no month available.
Derwent Publications Ltd., London, J6 2007772 (Alps Electric KK.), Jan. 14, 1987, (Abstract).
Gross et al. "Laser direct–write metallization in thin palladium acetate films" *J. Appl. Phys.* 61(4) 1628–1632 1987, no month available.
Al–Ismail et al. "Some experimental results on thin polypropylene films loaded with finely–dispersed copper" *Journal of Materials Science* 415–418 1987, no month available.
Baufay et al. "Optical self–regulation during laser–induced oxidation of copper" *J. Appl. Phys* 61(9) 4640–4651 1987, no month available.
Lindsey, J.S. et al. Rothemund and Adler–Longo Reactions Revisited: Synthesis of Tetraphenylporphyrins under Equilibrium Conditions *J. Org. Chem.* 52 pp. 827–836 1987, no month available.
Derwent Publications Ltd., London, JA 0284478 (Sanyo Chem Ind Ltd.), Dec. 15, 1986 (Abstract).
Abstract of patent, JP 61251842 1986, no month available.
Database WPI, Derwent Publications Ltd., London, GB; SU, A, 1098210 (Kutulya L A) Jun. 23, 1986.
Abstract of patent, JP 61–97025 1986, no month available.
Abstract of patent, JP 61–87760 1986, no month available.

Derwent Publications Ltd., London, DL 0234731 (Karl Marx Univ. Leipzig), Apr. 9, 1986. (Abstract).
Derwent World Patents Index, SU 1219612 (AS USSR NON–AQ SOLN) Mar. 23, 1986.
Derwent Publications, Ltd., London, J6 1041381 (Osaka Prefecture), Feb. 27, 1986 (Abstract).
Dialog, JAPIO, JP 61–034057 (Ciba Geigy AG) Feb. 18, 1986.
Derwent World Patents Index, JP 61027288 (sumitomo Chem Ind KK) Feb. 6, 1986.
Sakai et al. "A Novel and Practical Synthetic Method of 3(2H)–Furanone Derivatives," *J. Heterocyclie Chem.* 23 pp. 1199–1201 1986, no month available.
Jellinek, H.H.G. et al. "Evolution of H2O and CO2 During the Copper–Catalyzed Oxidation of Isotactic Polypropylene," *J. Polymer Sci.* 24 389–403 1986, no month available.
Jellinek, H.H.G. et al. "Diffusion of Ca2+ Catalysts from Cu–Metal Polymer or Cu–Oxide/Polymer Interfaces into Isotactic Polypropylene," *J. Polymer Sci.* 24 503–510 1986, no month available.
John J. Eisch and Ramiro Sanchez "Selective, Oxophilic Imination of Ketones with Bis (dichloroaluminum) Phenylimide" *J. Org. Chem.* 51(10) 1848–1852 1986, no month available.
Derwent Publications Ltd., London, J6 0226575 (Sumitomo Chem Ind Ltd.), Oct. 11, 1985 (Abstract).
Abstract of patent, JP 60–156761 1985, no month available.
Derwent World Patents Index DE 3443565 (Mitsubishi Yuka Fine Che. et al.) Jul. 11, 1985. abstract.
Derwent Publications Ltd., London, J,A, 0011451 (Fugi Photo Film KK), Jan. 21, 1985. (Abstract).
Derwent Publications, Ltd., London J6 0011449—A (Taoka Chemical KK) Jan. 21, 1985 (Abstract).
Derwent World Patents Index JP 60–008088 (Mitsubishi Paper Mills Ltd.) Jan. 16, 1985. abstract.
Roos, G. et al. "Textile applications of photocrosslinkable polymers" *Chemical Abstracts* 103 57 [No. 103:23690j] 1985, no month available.
Beck, M.T., et al. Mechanism of the autophotosensitized formulation of porphyrins in the reaction of pyrrole and m–disulfonated *Chemical Abstracts* 198 5:45362 1985, no month available.
Derwent World Patents Index, EP 127574 (Ciba Geigy AG), Dec. 5, 1984.
Derwent Publications Ltd., London, JP 0198187 (Canon KK), Nov. 9, 1984. (Abstract).
Derwent Publications Ltd., London, J,A, 0169883 (Ricoh KK), Sep. 25, 1984. (Abstract).
Derwent Publications Ltd., London, JA 0169883 (Ricoh KK), Sep. 25, 1984 (Abstract).
Derwent Publications Ltd., London, JA 0198187 (Canon KK), Nov. 9, 1984 (Abstract).
Derwent Publications Ltd., London, J,A, 0053563 (Dainippon Toryo KK), Mar. 28, 1984. (Abstract).
Derwent Publications Ltd., London, J,A, 0053562 (Dainippon Toryo KK), Mar. 28, 1984. (Abstract).
Abstract of Patent, JA 0053563 (Dainippon Toryo KK), Mar. 28, 1984 (Abstract).
Abstract of Patent, JA 0053562 (Dainippon Toryo KK), Mar. 28, 1984 (Abstract).
Derwent Publications Ltd., London, J,A, 0051961 (Dainippon Toryo KK), Mar. 26, 1984). (Abstract).
Abstract of Patent, JA 0051961 (Dainippon Toryo KK), Mar. 26, 1984 (Abstract).

Saenger, W. "Structural Aspects of Cyclodextrins and Their Inclusion Complexes" *Inclusion Compounds—Structural Aspects of Inclusion Compounds formed by Organic Host* 2 231–259 1984, no month available.

Szejtli "Industrial Applications of Cyclodextrins" *Inclusion Compounds: Physical Prop. & Applns* 3 331–390 1984, no month available.

Kano et al. "Three–Component Complexes of Cyclodextrins. Exciplex Formation in Cyclodextrin Cavity," *J. Inclusion Phenomena* 2 pp. 737–746 1984, no month available.

Suzuki et al. "Spectroscopic Investigation of Cyclodextrin Monomers, Derivatives, Polymers and Azo Dyes," *J. Inclusion Phenomena* 2, pp. 715–724 1984, no month available.

Abstract of Patent, JA 0222164 (Ricoh KK), Dec. 23, 1983 (Abstract).

Abstract of patent, JP 58211426 (Sekisui Plastics KK), (Dec. 8, 1983).

Derwent Publications, Ltd., London, EP 0072775 (Ciba Geigy AG), Feb. 23, 1983 (Abstract).

van Beek, H.C.A "Light–Induced Colour Changes in Dyes and Materials" *Color Res. and Appl.* 8 176–181 1983, no month available.

Connors, K.A. "Application of a stoichiometric model of cyclodextrin complex formation" *Chemical Abstracts* 98 598 [No. 98:53067g] 1983, no month available.

Abstract of Patent, EP 0065617 (IBM Corp.), Dec. 1, 1982 (Abstract).

Derwent Publications Ltd., London, J,A, 0187289 (Honshu Paper Mfg KK), Nov. 17, 1982. (Abstract).

Abstract of Patent, JA 0187289 (Honsho Paper Mfg KK), Nov. 17, 1982 (Abstract).

Abstract of Patent, JA 0185364 (Ricoh KK), Nov. 15, 1982 (Abstract).

Derwent Publications, Ltd., London J5 7139146 (Showa Kako KK) Aug. 27, 1982 (abstract).

Abstract of Patent, JA 0090069 (Canon KK), Jun. 4, 1982 (Abstract).

Derwent Publications, Ltd., London, JA 0061785 (Nippon Senka KK), Apr. 14, 1982 (Abstract).

Fischer, "Submicroscopic contact imaging with visible light by energy transfer" *Appl. Phys. Letter* 40(3) 1982, no month available.

Abstract of Patent, JA 0010659 (Canon KK), Jan. 20, 1982 (Abstract).

Abstract of Patent, JA 0010661 (Canon KK), Jan. 20, 1982 (Abstract).

Christen "Carbonylverbindungen: Aldehyde und Ketone," *Grundlagen der Organischen Chemie* 255 1982, no month available.

Derwent Publications Ltd., London, J,A, 0155263 (Canon KK), Dec. 1, 1981. (Abstract).

Abstract of Patent, JA 0155263 (Canon KK), Dec. 1, 1981 (Abstract).

Abstract of Patent, JA 0147861 (Canon KK), Nov. 17, 1981 (Abstract).

Derwent Publications Ltd., London, J,A, 0143273 (Canon KK), Nov. 7, 1981. (Abstract).

Abstract of Patent, JP 56143272 (Canon KK), Nov. 7, 1981 (Abstract).

Patent Abstracts of Japan, JP 56143274 (Canon Inc.) Nov. 7, 1981, abstract.

Abstracts of Patent, JA 0136861 (Canon KK), Oct. 26, 1981 (Abstract).

Abstract of Patent, JA 6133378 (Canon KK), Oct. 19, 1981 (Abstract).

Abstract of Patent, JA 6133377 (Canon KK), Oct. 19, 1981 (Abstract).

Abstract of Patent, JA 6093775 (Canon KK), Jul. 29, 1981 (Abstract).

Derwent Publications Ltd., London, J,A, 0008135 (Ricoh KK), Jan. 27, 1981. (Abstract).

Derwent Publications Ltd., London, J,A, 0004488 (Canon KK), Jan. 17, 1981. (Abstract).

Abstract of Patent, JA 0004488 (Canon KK), Jan. 17, 1981 (Abstract).

Kirk–Othmer "Metallic Coatings," *Encyclopedia of Chemical Technology* 15 241–274 1981, no month available.

Komiyama et al. "One–Pot Preparation of 4–Hydroxychalcone β–Cyclodextrin as Catalyst," *Makromol. Chem.* 2 733–734 1981, no month available.

Derwent Publications, Ltd., London CA 1086–719 (Sherwood Medical) Sep. 30, 1980 (abstract).

Derwent Publications Ltd., Database WPI, JP 55 113036 (Ricoh KK), Sep. 1, 1980.

Rosanske et al. "Stoichiometric Model of Cyclodextrin Complex Formation" *Journal of Pharmaceutical Sciences* 69(5) 564–567 1980, no month available.

Semple et al. "Synthesis of Functionalized Tetrahydrofurans," *Tetrahedron Letters* 81 pp. 4561–4564 1980, no month available.

Kirk–Othmer "Film Deposition Techniques," *Encyclopedia of Chemical Technology* 10 247–283 1980, no month available.

Derwent World Patents Index, Derwent Info. Ltd., JP 54158941 (Toyo Pulp KK), Dec. 15, 1979. (Abstract).

Derwent World Patents Index, JP 54117536 (Kawashima F) Sep. 12, 1979.

Derwent Publications Ltd., London, J,A, 0005422 (Fuji Photo Film KK), Jan. 16, 1979. (Abstract).

Drexhage et al. "Photo–bleachable dyes and processes" *Research Disclosure* 85–87 1979, no month available.

"Color imaging devices and color filter arrays using photo–bleachable dyes" *Research Disclosure* 22–23 1979, no month available.

Wolff, N.E., et al. "Electrophotography" *Kirk–Othmer Encyclopedia of Chemical Technology* 8 794–826 1979, no month available.

Derwent Publications Ltd., London, J,A, 0012037 (Pentel KK), Jan. 29, 1977. (Abstract).

Abstract of Patent, JA 0012037 (Pentel KK), Jan. 29, 1977 (Abstract).

Jenkins, P.W. et al. "Photobleachable dye material" *Research Disclosure* 18 [No. 12932] 1975, no month available.

Lamberts, R.L. "Recording color grid patterns with lenticules" *Research Disclosure* 18–19 [No. 12923] 1975, no month available.

Karmanova, L.S. et al. "Light stabilizers of daytime fluorescent paints" *Chemical Abstracts* 82 147 [No. 59971p] 1975, no month available.

Prokopovich, B. et al. "Selection of effective photoinducers for rapid hardening of polyester varnish PE–250" *Chemical Abstracts* 83 131 [No. 81334a] 1975, no month available.

"Variable Contrast Printing System" *Research Disclosure* 19 [No. 12931] 1975, no month available.

Lakshman "Electronic Absorption Spectrum of Copper Formate Tetrahydrate" *Chemical Physics Letters* 31(2) 331–334 1975, no month available.

Derwent Publications, Ltd., London J4 9131–226 (TNational Cash Register C) Dec. 16, 1974 (abstract).

Chang, I.F., et al. "Color Modulated Dye Ink Jet Printer" *IBM Technical Disclosure Bulletin* 17(5) 1520–1521 1974, no month available.

"Darocur 1173: Liquid Photoiniator for Ultraviolet Curing of Coatings" 1974, no month available.

Hosakawa et al. "Ascofuranone, an antibiotic from Ascochyta," Japan Kokai 73 91,278 (Nov. 28, 1973) *Merck Index* 80 p. 283; abstract 94259t 1974, no month available.

Abstract of patent, NL 7112489 (Dec. 27, 1971).

Gafney et al. "Photochemical Reactions of Copper (II)—1, 3–Diketonate Complexes" *Journal of the Americqal Chemical Society* 1971, no month available.

Derwent Publications, Ltd., London SU 292698–S Jan. 15, 1971 (abstract).

Derwent World Patents Index,CS 120380 (Kocourek, Jan) Oct. 15, 1966.

Tsuda, K. et al. Vinyl Polymerization. CXLVI. The influence of dibenzoyl disulfide derivatives on radical polymerizations *Chemical Abstract* 196 6:29198 1966, no month available.

R.T. Morrison & R.N. Boyd *Organic Chemistry* pp. 174;707–711 1959, no month available.

Rigdon, J.E. "In Search of Paper that Spies Can't Copy" *Wall Street Journal,* no date available.

Chatterjee,S. et al. "Photochemistry of Carbocyanine Alkyltriphenylborate Salts: Intra–Ion–Pair Electron Transfer and the Chemistry of Boranyl Radicals" *J. Am. Chem. Soc.* 112 6329–6338, no date available.

"Assay—Physical and Chemical Analysis of Complexes" *AMAIZO,* no date available.

"Cyclodextrin" *AMAIZO,* no date available.

"Beta Cyclodextrin Polymer (BCDP)" *AMAIZO,* no date available.

"Chemically Modified Cyclodextrins" *AMAIZO,* no date available.

"Cyclodextrin Complexation" *American Maize Products Co.,* no date available.

"Monomers" *Scientific Polymer Products, Inc.,* no date available.

Suppan, Paul "Quenching of Excited States" *Chemistry and Light* 65–69, no date available.

Yamaguchi, H. et al. "Supersensitization Aromatic ketones as supersensitizers" *Chemical Abstracts* 53 107 (d), no date available.

Stecher, H. "Ultraviolet–absorptive additives in adhesives, lacquers and plastics," *Chemical Abstracts* 53 14579 (c), no date available.

Maslennikov, A.S. "Coupling of diazonium salts with ketones" *Chemical Abstracts* 60 3128e, no date available.

Derwent Publications Ltd., London, 4 9128022, no date available.

Abstract of Patent, JP 405195450, no date available.

Rose, Philip I. "Gelatin," *Encyclopedia of Chemical Technology* 7 488–513, no date available.

SUBPHTHALOCYANINE COLORANTS, INK COMPOSITIONS, AND METHOD OF MAKING THE SAME

CROSS-REFERENCE TO RELATED APPLICATIONS

This patent application claims the benefit of priority to U.S. provisional patent application No. 60/135,456, filed on May 24, 1999, and U.S. provisional patent application No. 60/175,653, filed on Jan. 12, 2000.

TECHNICAL FIELD

The present invention relates to new methods for making subphthalocyanine compounds. The present invention also relates to a family of new subphthalocyanine compounds. The new subphthalocyanine compounds may be used as a colorant, alone or in combination with one or more colorants. The present invention further relates to inks containing the new subphthalocyanine compounds.

BACKGROUND OF THE INVENTION

A variety of subphthalocyanine compounds and methods for making the same are known in the art. Most conventional methods for producing subphthalocyanine compounds typically require a high reaction temperature, usually in the range of about 200° C. to about 250° C., due to the use of solvents, such as 1-chloro-naphthalene. Further, most conventional methods produce subphthalocyanine compounds along with a variety of secondary products, which require extensive separation procedures in order to isolate the subphthalocyanine compound. In addition, the reaction yield for the production of subphthalocyanine compounds by most conventional methods is at most about 35%, and usually less than about 20%. Such reaction conditions result in high energy costs, potential damage to the environment due to environmentally-unfriendly solvents, and low yields, which in turn results in high costs for the subphthalocyanine compounds produced.

U.S. Pat. No. 5,864,044 issued to Van Lier et al. discloses methods of making subphthalocyanine compounds, wherein a solvent having a lower boiling point is used. Van Lier discloses the use of 1-chlorobenzene (b.p. 130° C.) as a suitable solvent for the production of subphthalocyanine compounds. However, 1-chlorobenzene is an environmentally unfriendly solvent currently under increased scrutiny by the U.S. Environmental Protection Agency. Although Van Lier discloses the production of subphthalocyanine compounds at yields of about 60%, the method uses an environmentally unfriendly solvent, which presents manufacturing problems in the U.S.

Although the prior art discloses methods of making subphthalocyanine compounds at yields of up to about 60%, higher yields are desired in order to cost-effectively produce subphthalocyanine compounds. Further, higher yields without the use of environmentally unfriendly solvents are more desirable.

Moreover, known subphthalocyanine compounds possess poor lightfastness properties, which prevent the compounds from being used as colorants in conventional ink sets. It is believed that the poor lightfastness of known subphthalocyanine compounds is primarily due to the high reactivity of the molecule in the excited state, as well as, the higher concentration of molecules in the excited state and the length of time in the excited state, when a sample of the molecule is exposed to light. As reported in "Synthesis and Nonlinear Optical, Photophysical, and Electrochemical Properties of Subphthalocyanines", del Rey et al., *J. Am. Chem. Soc.*, Vol. 120, No. 49 (1998), known subphthalocyanine compounds have an excited state lifetime of as much as 100 µsec. Other possible reasons for poor lightfastness and tendency to fade are (1) reaction with singlet oxygen, and (2) nucleophilic attack resulting in a loss of boron and/or substitution of a chromophore.

What is needed in the art is an improved method of making subphthalocyanine compounds, which uses an environmentally-friendly solvent, and at the same time, results in yields of greater than 50%. Further, what is also needed in the art is a new family of stable, subphthalocyanine compounds having improved lightfastness properties, which may be used as colorants, alone or in combination with one or more colorants.

SUMMARY OF THE INVENTION

The present invention addresses the needs described above by providing new methods of making subphthalocyanine compounds. The methods of the present invention may be used to produce known subphthalocyanine compounds, as well as, new families of subphthalocyanine compounds having superior light fastness properties disclosed herein.

The present invention is further directed to a new family of subphthalocyanine compounds having the following general formula:

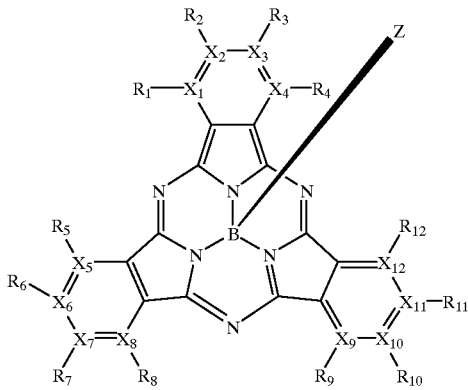

wherein $X_1$ to $X_{12}$ each independently represent carbon or nitrogen; $R_1$ to $R_{12}$ and Z each independently represent —H, a halogen, an alkyl group, a substituted alkyl group, an aryl group, a substituted aryl group, an alkoxide group, a phenoxy group, a substituted phenoxy group, an alkyl sulfide, an aryl sulfide, a nitrogen-containing group, a sulfonic acid, a sulfur-containing group or an ester group; and wherein when any one of $X_1$ to $X_{12}$ is nitrogen, the corresponding $R_1$ to $R_{12}$ represents the pair of electrons on the nitrogen atom. The subphthalocyanine compounds may be used as a colorant alone or in combination with one or more colorants.

The present invention also relates to colorant compositions having improved stability, wherein the colorant comprises one or more of the above-described subphthalocyanine compounds.

These and other features and advantages of the present invention will become apparent after a review of the following detailed description of the disclosed embodiments and the appended claims.

DETAILED DESCRIPTION OF THE INVENTION

The present invention is directed to methods of making subphthalocyanine compounds. The methods of the present invention may be used to produce known subphthalocyanine compounds, as well as, a new family of subphthalocyanine compounds disclosed herein. Unlike conventional methods of making subphthalocyanine compounds, the methods of the present invention utilize a reaction mechanism, which occurs at a temperature below about 180° C., while employing environmentally friendly solvents. In addition, the methods of the present invention produce subphthalocyanine compounds at a reaction yield of greater than about 50%, and up to about 94%.

One method of making subphthalocyanine compounds of the present invention may be given by the following reaction scheme:

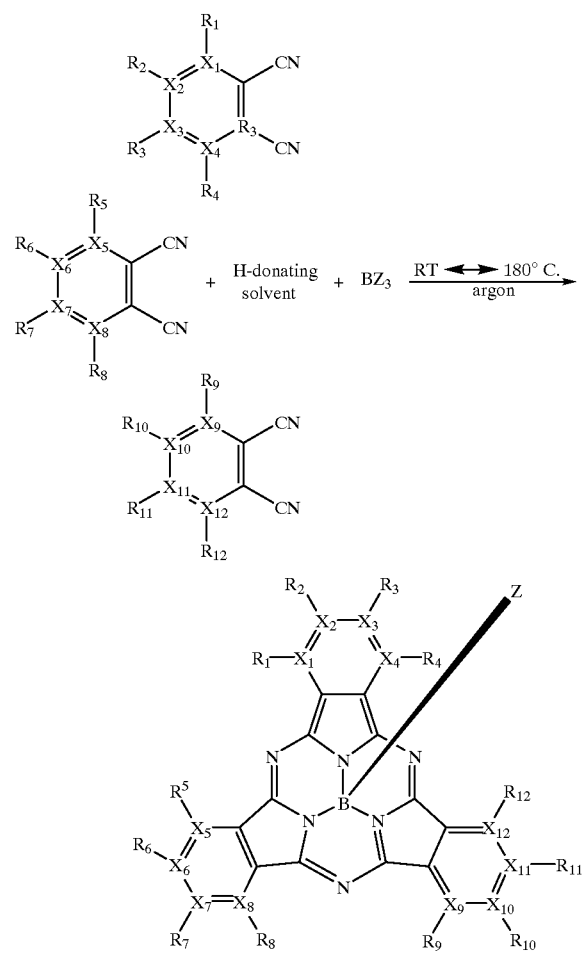

wherein $X_1$ to $X_{12}$ each independently represent carbon or nitrogen; $R_1$ to $R_{12}$ and Z each independently represent —H, a halogen, an alkyl group, a substituted alkyl group, an aryl group, a substituted aryl group, an alkoxide group, a phenoxy group, a substituted phenoxy group, an alkyl sulfide, an aryl sulfide, a nitrogen-containing group, a sulfonic acid, a sulfur-containing group, or an ester group; and wherein when any one of $X_1$ to $X_{12}$ is nitrogen, the corresponding $R_1$ to $R_{12}$ represents the pair of electrons on the nitrogen atom. The reaction may occur at a reaction temperature much lower than most conventional reaction methods. In one embodiment of the present invention, the method of making subphthalocyanine compounds takes place at a desired reaction temperature of from about 20° C. to about 180° C. More desirably, the reaction temperature is from about 50° C. to about 160° C. Even more desirably, the reaction temperature is from about 80° C. to about 150° C.

In a further embodiment of the present invention, the method of making subphthalocyanine compounds may be given by the following reaction scheme:

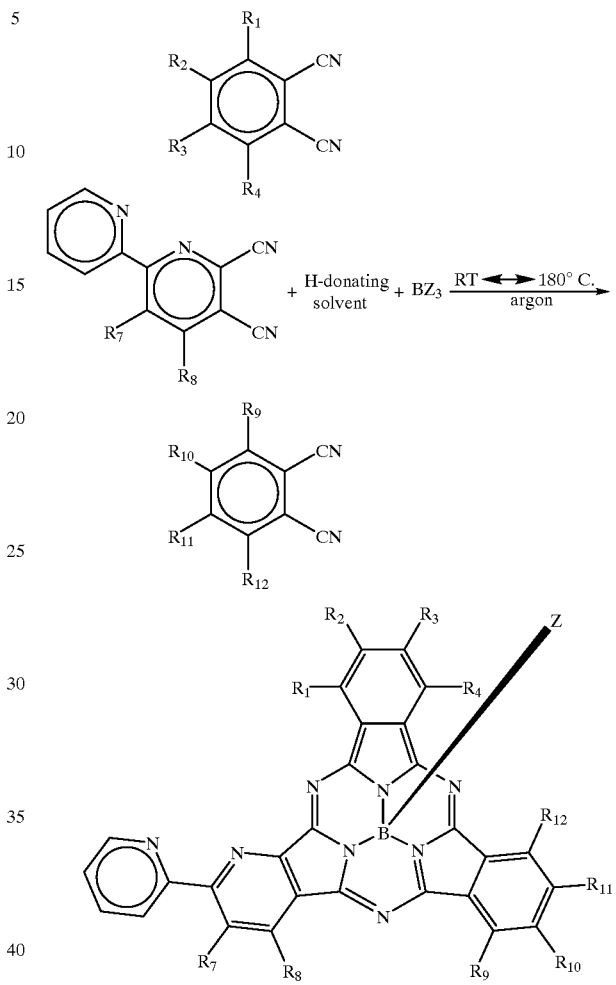

wherein $R_1$ to $R_4$, $R_7$ to $R_{12}$ and Z each independently represent —H, a halogen, an alkyl group, a substituted alkyl group, an aryl group, a substituted aryl group, an alkoxide group, a phenoxy group, a substituted phenoxy group, an alkyl sulfide, an aryl sulfide, a nitrogen-containing group, a sulfonic acid, a sulfur-containing group, or an ester group. The reaction may occur at a reaction temperature as discussed above, with the desired reaction temperature being from about 80° C. to about 150° C. The resulting subphthalocyanine compounds have a unique, unsymmetrical chemical structure, which enables "intramacrocyclic quenching," as well as, "intermacrocyclic quenching" with other molecules as described below.

The methods of the present invention use a variety of environmentally-friendly solvents. Desirably, the solvent comprises a "hydrogen-donating" solvent. As used herein, the term "hydrogen-donating" describes solvents, which are capable of donating a hydrogen atom during the above-described reactions. Hydrogen-donating solvents are distinguishable from hydrogen-containing solvents, such as benzene, 1-chloro-naphthalene and 1-chlorobenzene, which do not possess a hydrogen, which may be donated during the reaction mechanism of the present invention. Suitable hydrogen-donating solvents for use in the present invention may vary according to the reactants, reaction temperature, and other reaction parameters. Suitable hydrogen-donating solvents include, but are not limited to, substituted aromatic compounds; cyclohexadiene; alcohols, such as 2-propanol; ethers, such as petroleum ether, tetrahydrofuran, dioxane, and tetralene. Desirably, the solvent comprises o-xylene, m-xylene, p-xylene, toluene, or a substituted benzene, wherein the substituent comprises a hydrogen-containing moiety. More desirably, the solvent comprises p-xylene, toluene, or cumene. Even more desirably, the solvent comprises p-xylene or cumene.

The methods of the present invention produce a variety of subphthalocyanine compounds at yields of greater than about 50%. Desirably, the method of making subphthalocyanine compounds has a yield of greater than about 60%. More desirably, the method of making subphthalocyanine compounds has a yield of greater than about 70%. Even more desirably, the method of making subphthalocyanine compounds has a yield of greater than about 80%. Even more desirably, the method of making subphthalocyanine compounds has a yield of greater than about 85%. Even more desirably, the method of making subphthalocyanine compounds has a yield of greater than about 90%. Most desirably, the method of making subphthalocyanine compounds has a yield of greater than about 94%.

In the methods of the present invention, one or more reactants may be used in combination with one or more hydrogen-donating solvents. Suitable reactants include, but are not limited to, phthalonitrile, one or more substituted phthalonitriles, pyridine-2,3-dicarbonitrile, one or more substituted pyridine-2,3-dicarbonitriles, pyridine-3,4-dicarbonitrile, one or more substituted pyridine-3,4-dicarbonitriles, pyrazine-2,3-dicarbonitrile, one or more substituted pyrazine-2,3-dicarbonitriles, or a combination thereof. Substituted phthalonitrile compounds include phthalonitrile compounds having up to six moieties bonded to the aromatic ring of the phthalonitrile compound. Further, substituted pyridine-2,3-dicarbonitrile compounds include pyridine-2,3-dicarbonitrile compounds having up to three additional moieties bonded to the aromatic ring of the pyridine-2,3-dicarbonitrile compound. Substituted pyridine-3,4-dicarbonitrile compounds include pyridine-3,4-dicarbonitrile compounds having up to three additional moieties bonded to the aromatic ring of the pyridine-3,4-dicarbonitrile compound. Substituted pyrazine-2,3-dicarbonitrile compounds include pyrazine-2,3-dicarbonitrile compounds having up to two additional moieties bonded to the aromatic ring of the pyrazine-2,3-dicarbonitrile compound.

Suitable moieties on the above-referenced substituted reactants include, but are not limited to, halogens, alkyl groups, alkoxy groups, cyano groups, carboxylic acid groups, sulfur-containing groups, nitrogen-containing groups, and salts thereof. Suitable halogens include, but are not limited to, chlorine, bromine, fluorine, and iodine. Suitable alkyl groups include, but are not limited to, methyl groups, ethyl groups, and tert-butyl groups. Suitable alkoxy groups include, but are not limited to, methoxy groups and ethoxy groups. Suitable sulfur-containing groups include, but are not limited to, —$SC_8H_{17}$, —$SO_3H$, —$SO_3Na$, -$SO_3Cl$, and —$SO_3Cl^-$. Suitable nitrogen-containing groups include, but are not limited to, —$NO_2$, —$pyH^+$, —$NR_2$, and —$NR3$, wherein R represents —H, a halogen, an alkyl group, a substituted alkyl group, an aryl group, a substituted aryl group, an alkoxide group, a phenoxy group, a substituted phenoxy group, an alkyl sulfide, an aryl sulfide, a nitrogen-containing group, a sulfonic acid, a sulfur-containing group, or an ester group. Other suitable groups also include, but are not limited to, —$CO_2Na$.

In addition to the above reactants, one or more boron-containing compounds may be used in the methods of the present invention. Suitable boron-containing compounds include, but are not limited to, halogen-substituted boron compounds, such as boron trichloride, boron trifluoride, and boron tribromide. Other suitable boron-containing compounds include mixed boron compounds containing at least one halogen atom and at least one phenyl group. Such mixed boron compounds include, but are not limited to, $BCl_2Ph$, $BClPh_2$, $BBr_2Ph$, and $BBrPh_2$, wherein "Ph" represents a phenyl group.

In one embodiment of the present invention, subphthalocyanine compounds are produced using the reaction mechanism described below:

Step 1

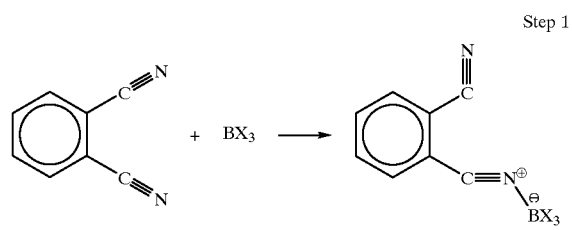

In step 1, X represents any Lewis base. Desirably, X is a halogen. More desirably, X is Cl.

Step 2

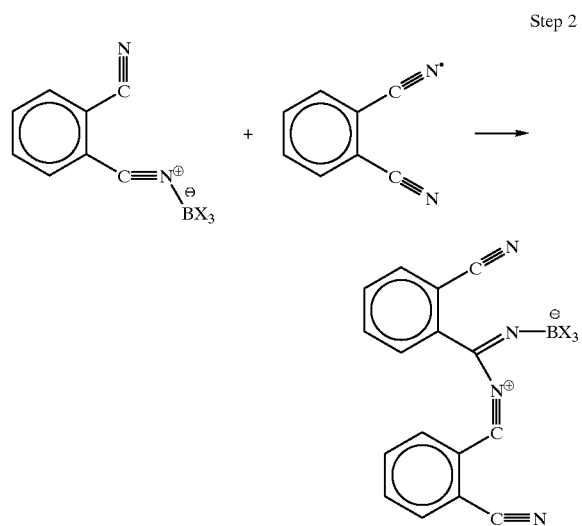

Step 3

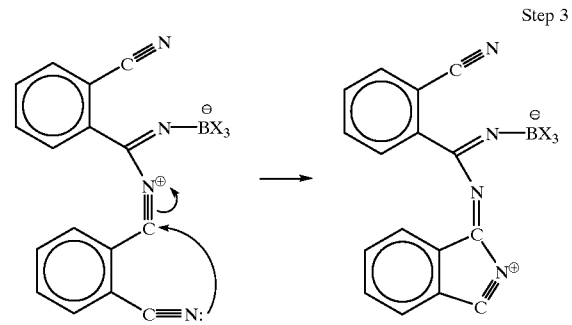

Step 4
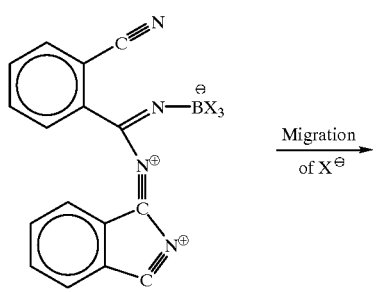 Migration of X⁻ →  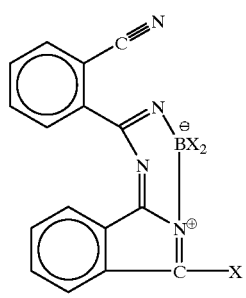
Step 5-8
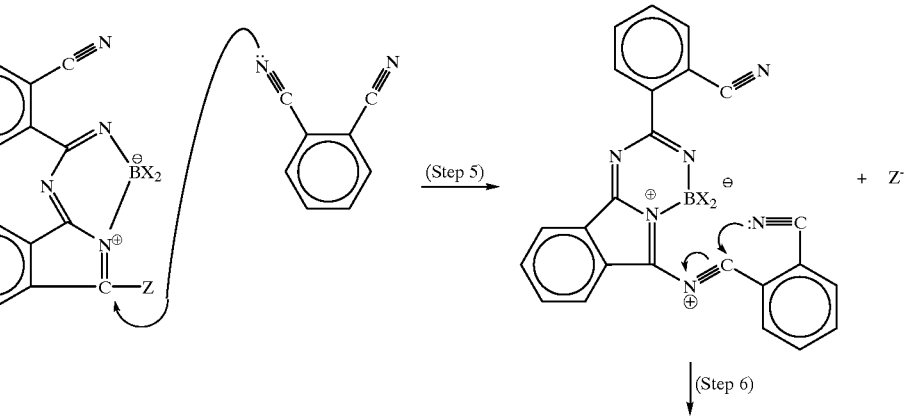
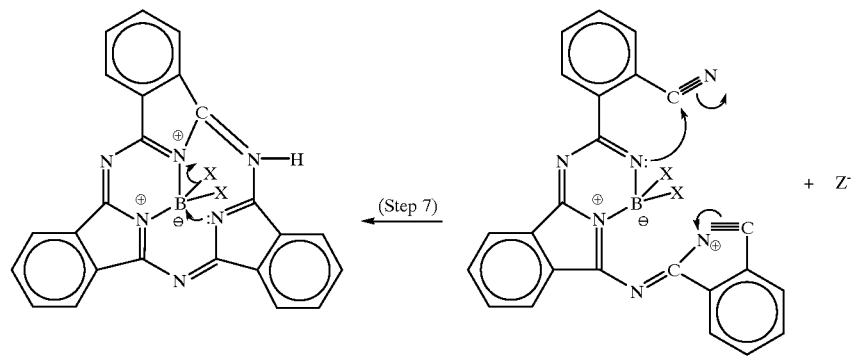
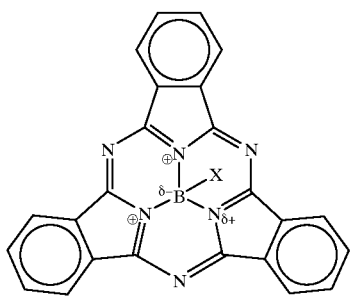 +2e⁻ (Step 9) → 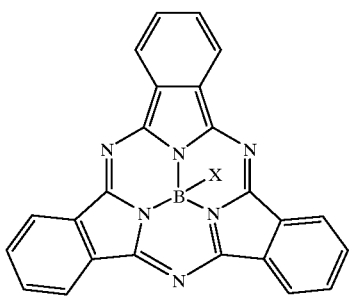

In step 9 two electrons are donated from hydrogen atoms of the hydrogen-donating solvent. The interaction of hydrogen atoms in the above mechanism may be described below:

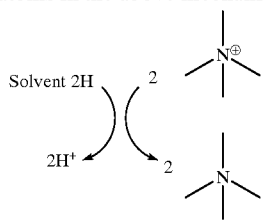

The hydrogen-donating solvent supplies two hydrogen atoms, which form two hydrogen ions and two electrons. The electrons balance the charge on two nitrogen atoms in the subphthalocyanine compound. The two hydrogen ions react with the Lewis base released by the boron compound to form two acid molecules as shown below.

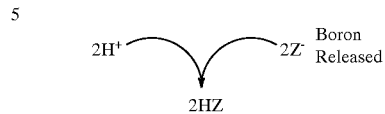

In a further embodiment of the present invention, subphthalocyanine compounds are produced using the following reaction mechanism. Steps 1–4 are the same steps as described above. Steps 5–11 are described below:

Steps 5-9

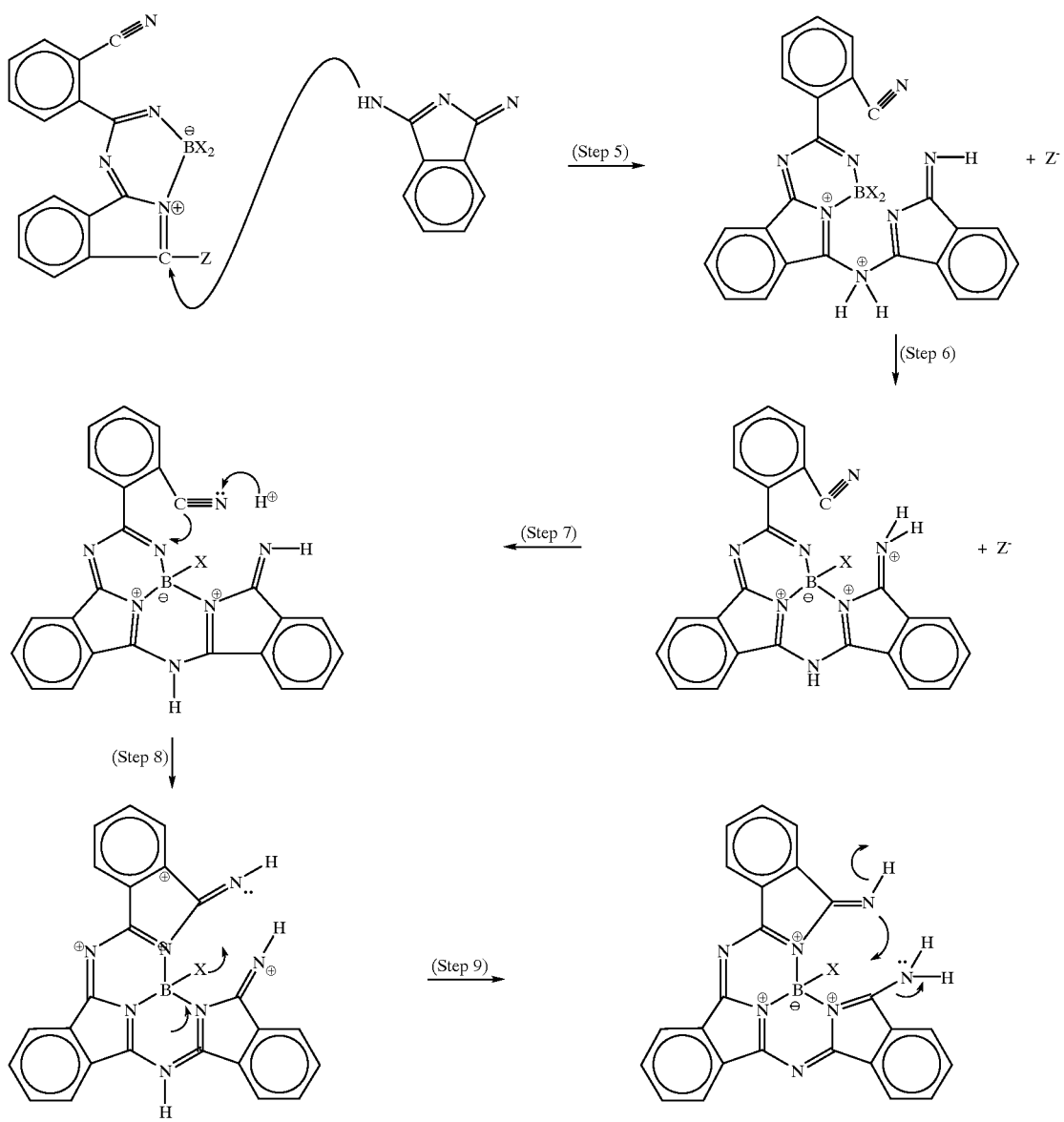

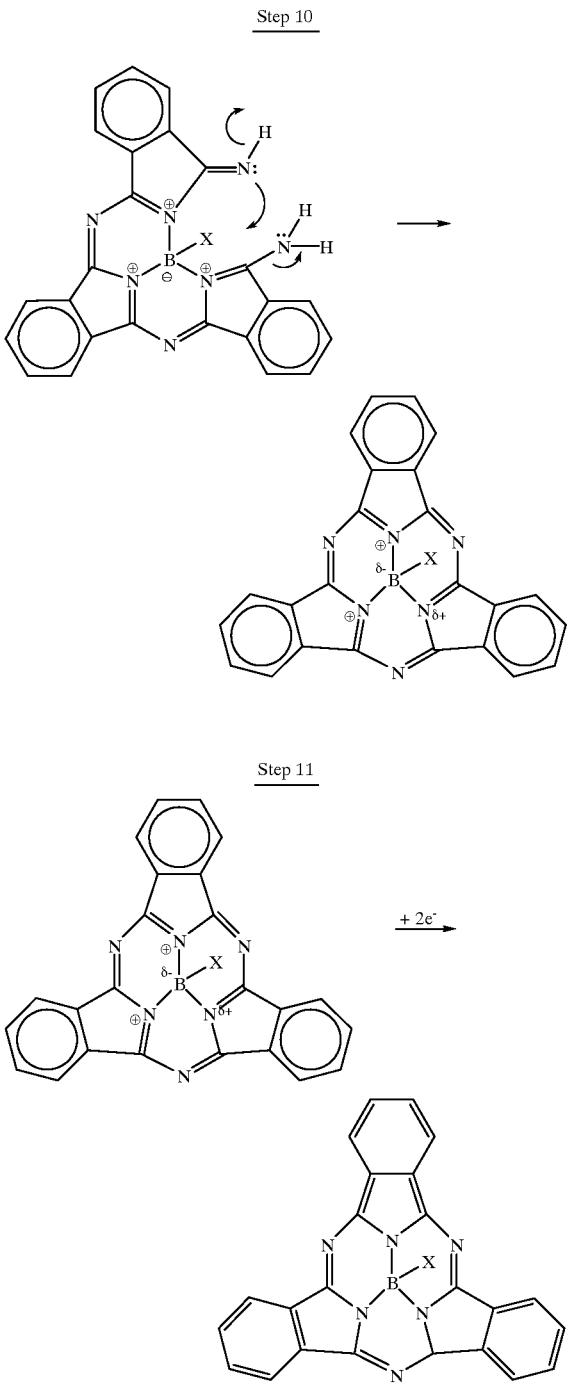

Step 10

Step 11

+ 2e⁻

In the above mechanisms, although phthalonitrile is shown as the reactant in Steps 1, 2, and 5 (of the first mechanism), it is to be understood that one or more unsubstituted phthalonitriles, substituted phthalonitriles, unsubstituted pyridine-2,3-dicarbonitriles, substituted pyridine-2,3-dicarbonitriles, unsubstituted pyridine-3,4-dicarbonitriles, substituted pyridine-3,4-dicarbonitriles, or a combination thereof may be used in Steps 1, 2, and 5 of the reaction mechanisms described above. Further, as shown in the second mechanism, a "capped" phthalonitrile may be used as a reactant. In this embodiment, the capped phthalonitrile may be formed by the following reaction:

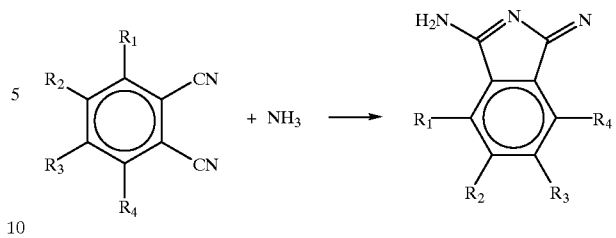

As in the first mechanism, the hydrogen-donating solvent supplies two electrons from hydrogen atoms in the solvent as shown in Step 11.

The present invention is further directed to a new family of subphthalocyanine compounds having the following general formula:

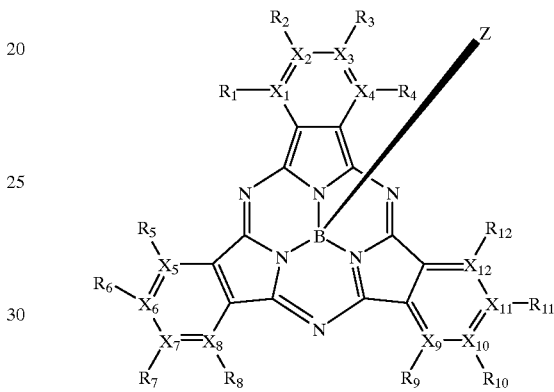

wherein $X_1$ to $X_{12}$ each independently represent carbon or nitrogen; $R_1$ to $R_{12}$ and Z each independently represent —H; a halogen; an alkyl group containing up to about 12 carbon atoms; a substituted alkyl group containing up to about 18 carbon atoms along the alkyl backbone; an aryl group; a substituted aryl group; an alkoxide group containing up to about 12 carbon atoms; a phenoxy group; a substituted phenoxy group; an alkyl sulfide containing up to about 8 carbon atoms; an aryl sulfide; a nitrogen-containing group; a sulfonic acid; a sulfur-containing group; a lanthanide-containing group; —OR', —NR"R", or —SR', wherein R' and R" each independently represent an alkyl group containing up to about 8 carbon atoms, a substituted alkyl group containing up to about 12 carbon atoms along the alkyl backbone, an aryl group, or a substituted aryl group; and wherein when any one of $X_1$ to $X_{12}$ is nitrogen, the corresponding $R_1$ to R12 represents the pair of electrons on the nitrogen atom. Desirably, $R_1$ to $R_{12}$ each independently represent —H, a halogen, an alkyl group containing up to about 8 carbon atoms, a nitrogen-containing group, a sulfur-containing group, or a lanthanide-containing group. More desirably, $R_1$ to $R_{12}$ each independently represent —H, chlorine, bromine, fluorine, iodine, a tert-butyl group, —NO$_2$, —SC$_8$H$_{17}$, —SO$_3$H, —SO$_3$Na, —SO$_2$Cl, —SO$_3^-$pyH$^+$, or a Eu-containing moiety. Even more desirably, $R_1$ to $R_{12}$ each independently represent —H, chlorine, bromine, fluorine, or iodine.

Suitable Z substituents may be selected from a variety of substituents, which provide desirable properties to the resulting subphthalocyanine compound. Desirably, Z comprises a moiety, which stabilizes the subphthalocyanine compound; a moiety, which renders the subphthalocyanine compound water soluble; or a moiety, which stabilizes and renders the subphthalocyanine water soluble. Examples of suitable Z include, but are not limited to, a hydroxyl group; a halogen; an alkyl group containing up to about 12 carbon atoms; an alkoxy group containing up to about 12 carbon atoms; an ether group; a polyol group; an aromatic group; a substitute aromatic group; a nitrogen-containing group; a sulfur-containing group; a lanthanide-containing group; —OR', —NR'R", or —SR', wherein R and R" each independently represent an alkyl group containing up to about 8 carbon atoms, a substituted alkyl group containing up to about 8 carbon atoms, an aryl group, or a substituted aryl group. Desirably, Z comprises one of the following moieties:

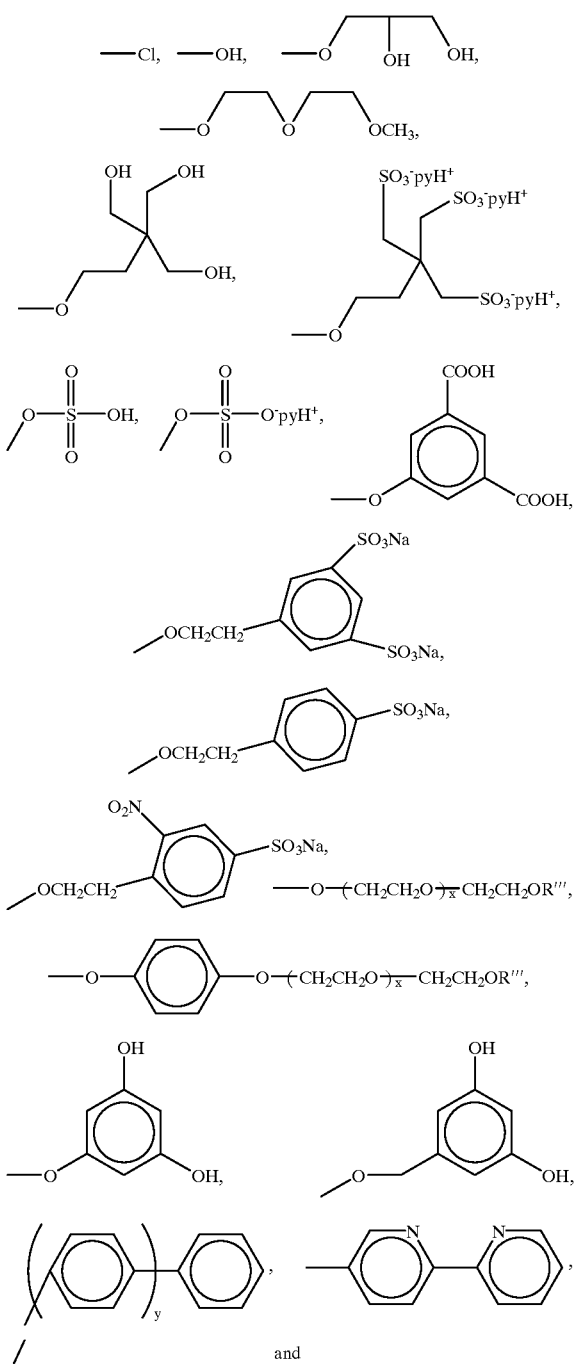

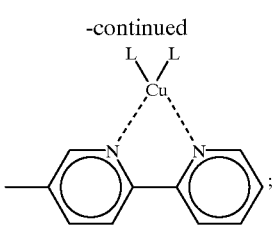

where x is an integer from 3 to 30, y is from 0 to 6, R'" is a hydrogen or an alkyl group having up to six carbon atoms, and L is acetate; halogens; ethylene diamine; compounds having the following structure, $H_2N(CH_2)_xNH_2$, wherein x is from 2 to 8; propionate; nitrate; or oxalate.

By selecting particular "R" and "Z" groups, subphthalocyanine compounds having superior lightfastness properties may be produced. In one embodiment of the present invention, subphthalocyanine compounds having superior lightfastness properties are produced; these compounds have the above general formula, wherein $X_1$ to $X_{12}$ each independently represent carbon or nitrogen; $R_1$ to $R_{12}$ each independently represent —H, a halogen, or —SR'; and Z represents a halogen, an aryl group, a substituted aryl group, a pyridine group, a substituted pyridine group,—OR', —NR'R", or —SR', wherein R' and R" each independently represent an alkyl group, a substituted alkyl group, an aryl group, or a substituted aryl group.

In a further embodiment of the present invention, subphthalocyanine compounds having the above general formula are produced, wherein $X_1$ to $X_{12}$ each independently represent carbon or nitrogen; $R_1$ to $R_{12}$ each independently represent —H, a halogen, or —SR'; and Z is desirably a phenyl group, an aryl group, or a substituted aryl group. In this embodiment, the phenyl group, aryl group, or substituted aryl group prevents a photochemical 1,3 shift of the axial ligand as shown in the example mechanism below:

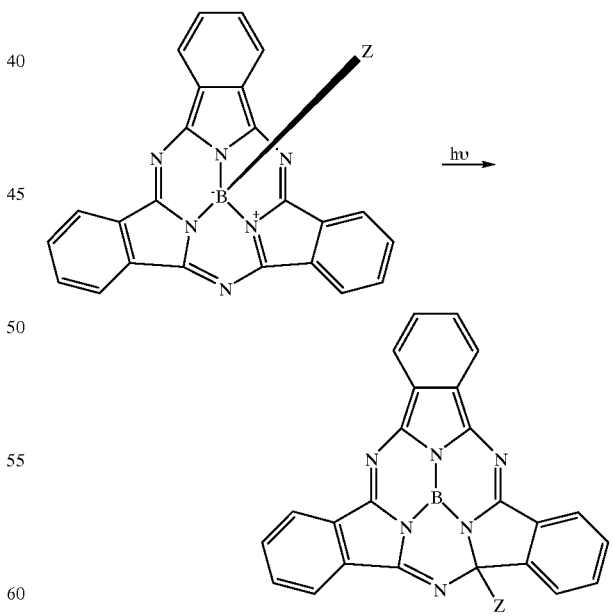

The superior lightfastness property of a given subphthalocyanine compound may be measured by the "Subphth.-Lightfastness Test" described herein. The Subphth.-Lightfastness Test used in the present invention measures the percent change in absorption of a $5\times10^{-5}$ M concentration solution of the subphthalocyanine compound in o-xylene, and is given by the following equation:

$$\%\Delta A=[(P_0-P_{144})/P_0]\times 100$$

wherein $P_0$ represents an absorption value at time zero (i.e., at the start of the test) and P144 represents an absorption value after 144 hours of exposure to a standard fluorescent lamp (i.e., Sylvania Cool White, 115 W, Model No. F48T12) placed about six feet from the subphthalocyanine compound. Desirably, the subphthalocyanine compound of the present invention has a Subphth.-Lightfastness Test value of less than about 15%. More desirably, the subphthalocyanine compound of the present invention has a Subphth.-Lightfastness Test value of less than about 12%. Even more desirably, the subphthalocyanine compound of the present invention has a Subphth.-Lightfastness Test value of less than about 10%.

As shown by the general formula above, the present invention is directed to a number of new subphthalocyanine compounds. Subphthalocyanine compounds of the present invention include, but are not limited to, the following compounds given below, wherein

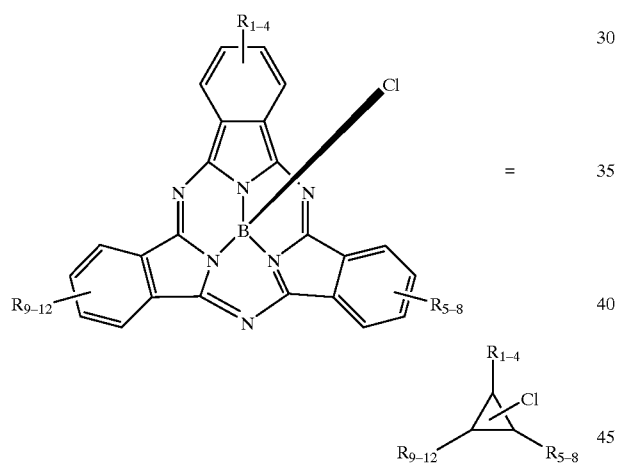

and wherein $R_{1-4}$ represents $R_1$ to $R_4$, $R_{5-8}$ represents $R_5$ to $R_8$, and $R_{9-12}$ represents $R_9$ to $R_{12}$:

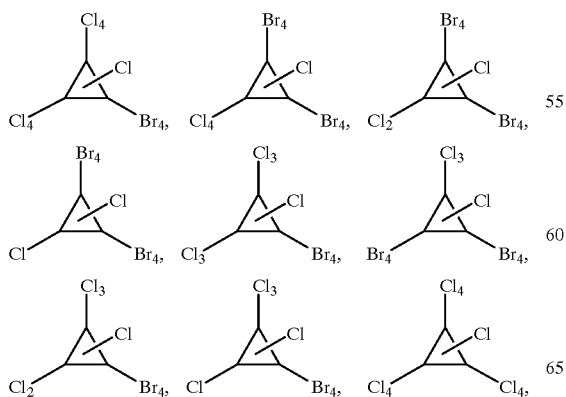

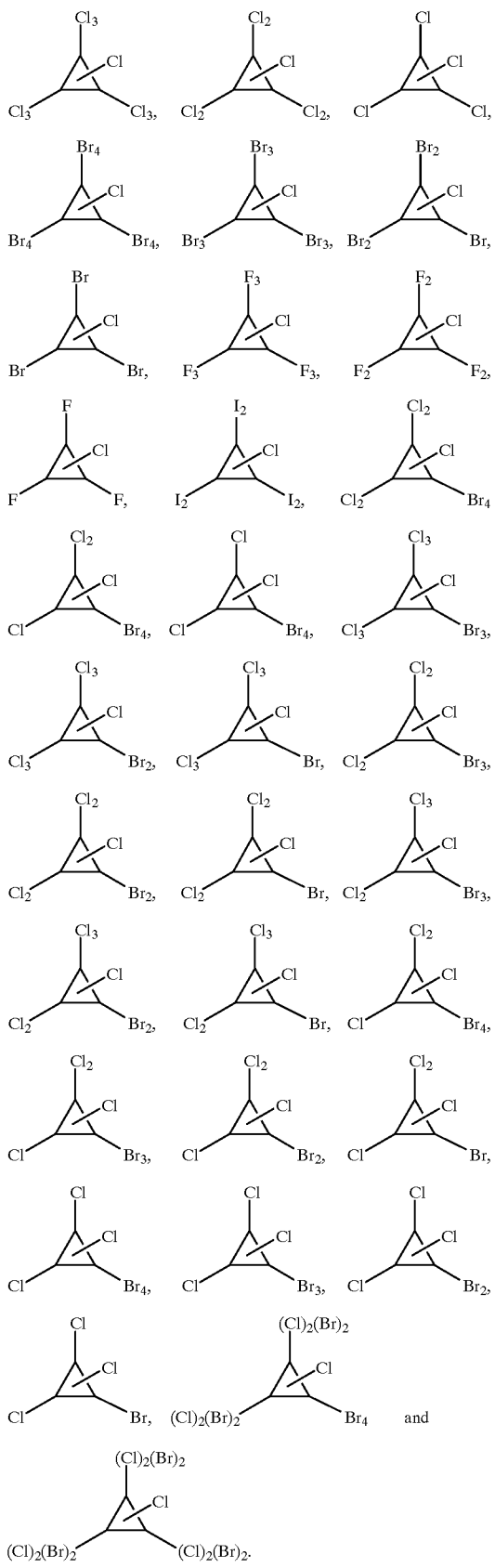

It is believed that the new subphthalocyanine compounds of the present invention possess superior lightfastness properties due to their reduced time in the excited state, as well as, their lower probability of being in the excited state. The presence of one or more substituents having high "Z" values (i.e., atomic number) on the aromatic rings of the compounds produces a "heavy atom effect," also known as "spin orbital coupling," which enables the distribution of vibrational energy at an excited state, resulting from exposure to light, intramolecularly. This "intramolecular quenching" of the molecule results in rapid quenching of the excited state back to the ground state. The net effect being a much smaller concentration of excited state species at any one time. A general discussion of "heavy atom effect" and "spin orbital coupling" may be found in the *Handbook of Photochemistry* (Murov et al.), $2_{nd}$ ed., Section 16, entitled "Spin-Orbit Coupling", pages 338–341 (1993), the entirety of which is incorporated herein by reference.

In one embodiment of the present invention, subphthalocyanine compounds having superior lightfastness are formed, wherein one or more "R" and/or "Z" groups have a spin-orbital coupling constant, $\iota_j$, of greater than about 500. Suitable "R" and/or "Z" groups have a spin-orbital coupling constant of greater than about 500 include, but are not limited to, chlorine ($\iota_j$=587), europium ($\iota_j$=1469), bromine ($\iota_j$=2460), and iodine ($\iota_j$=5069). Desirably, the subphthalocyanine compounds of the present invention contain one or more "R" and/or "Z" groups, which have a spin-orbital coupling constant, $\iota_j$, of greater than about 500. More desirably, the subphthalocyanine compounds of the present invention contain one or more "R" and/or "Z" groups, which have a spin-orbital coupling constant, $\iota_j$, of greater than about 1000. Even more desirably, the subphthalocyanine compounds of the present invention contain one or more "R" and/or "Z" groups, which have a spin-orbital coupling constant, $\iota_j$, of greater than about 1400.

As discussed above, it is believed that adding one or more substituents having high "Z" values (i.e., atomic number) onto the aromatic rings of the subphthalocyanine compounds produces "intramolecular quenching" of the molecule. In addition to "intramolecular quenching" of the subphthalocyanine compound, "intermolecular quenching" of the subphthalocyanine compound may be accomplished by associating one or more quenching compounds with the subphthalocyanine compound. An example of "intermolecular quenching" is shown in the structure below:

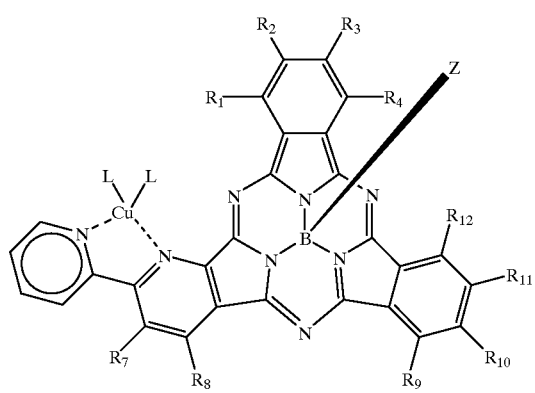

wherein a copper compound forms a coordinate covalent bond with two pair of electrons present on nitrogen atoms in close proximity to one another within the subphthalocyanine compound. A further example of "intermolecular quenching" is shown in the subphthalocyanine complex below:

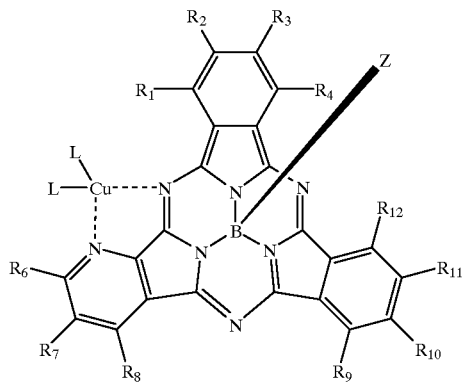

wherein a copper compound forms a coordinate covalent bond with two pair of electrons present on nitrogen atoms in close proximity to one another within the subphthalocyanine compound. In the $Cu(L)_2$ compound, "L" may be any moiety capable of complexing with the copper atom. Suitable "L" moieties include, but are not limited to, acetate; halogens; ethylene diamine; and compounds having the following structure, $H_2N(CH_2)_xNH_2$, wherein x is from 2 to 8; propionate; nitrate; and oxalate. It should be noted that compounds other than $Cu(L)_2$ may be used as a quenching moiety. Other compounds include, but are not limited to, other complexing transition metals and compounds containing a transition metal.

The above-described subphthalocyanine compound-containing complexes having "intramolecular quenching" and "intermolecular quenching" may be formed by reacting a subphthalocyanine compound with one or more complexing transition metals and compounds containing a transition metal. One method of reacting the above-described subphthalocyanine compounds with the quenching moiety is to simply mix the materials, add the mixture to a solvent, and allow the mixture to react at room temperature. Suitable solvents include, but are not limited to, dimethyl sulfoxide and dimethyl formamide. In some cases, the reaction may take place at a reaction temperature of up to about 100° C.

A variety of subphthalocyanine compound-containing complexes may be formed by the above-described reaction mechanism. By selecting particular "R" groups, axial ligand Z, and quenching groups, subphthalocyanine compound-containing complexes having superior lightfastness properties may be produced. Examples of possible subphthalocyanine compound-containing complexes include, but are not limited to,

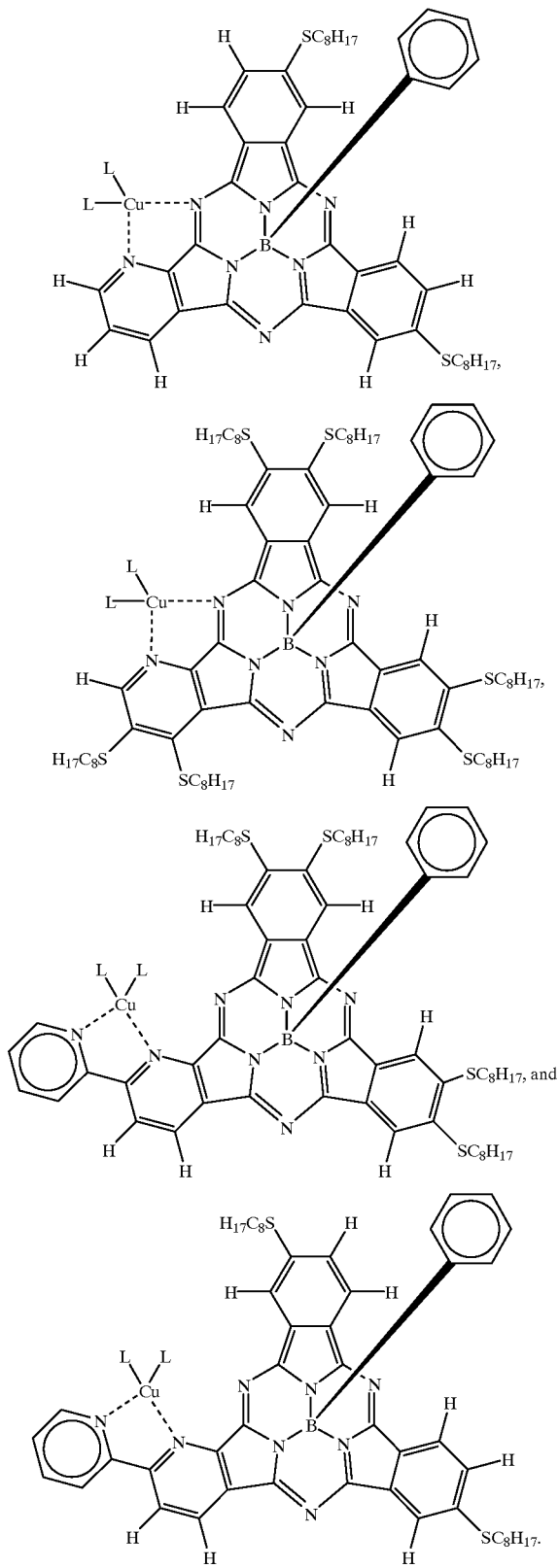

Other desired subphthalocyanine compound-containing complexes include, but are not limited to, the above compounds wherein the axial ligand comprises a substituted aryl having the formula

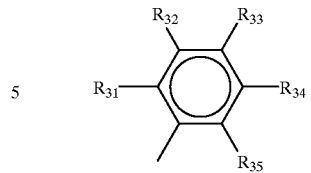

wherein $R_{31}$ to $R_{35}$ each independently represent —H, a halogen, —$NO_2$, a carboxy group, or a carbonyl group.

One example of a subphthalocyanine compound-containing complexes wherein the axial ligand contains a quenching compound is given below.

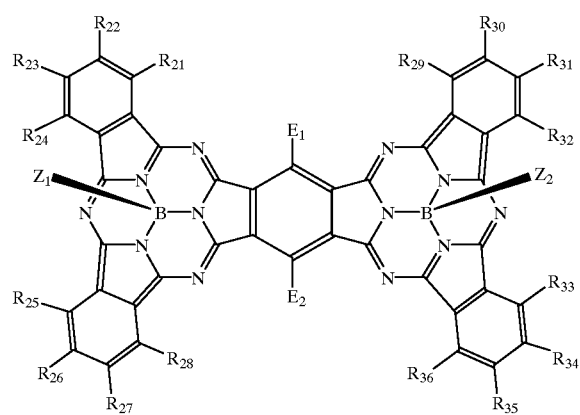

It should be noted that the above compound is only one example of many subphthalocyanine compound-containing complexes of the present invention, wherein the axial ligand contains a quenching compound.

In a further embodiment of the present invention, two subphthalocyanine compounds are reacted with a third reactant to obtain a compound having the following general formula:

wherein $R_{21}$, to $R_{36}$, $Z_1$, and $Z_2$ each independently represent moieties as described above with respect to $R_1$ to $R_{12}$ and Z. In the formation of the above compound, the third reactant may be selected from 1,3,4,6-tetracyanobenzene or 1,3,4,6-tetracyanobenzene further substituted with one or more electron-withdrawing groups, $E_1$ and $E_2$. Suitable electron-withdrawing groups "E" include, but are not limited to, a halogen; —NO$_2$, a halogen, —OR', and —CO$_2$R', wherein R' represents an alkyl group containing up to about 8 carbon atoms, a substituted alkyl group containing up to about 12 carbon atoms along the alkyl backbone, an aryl group, or a substituted aryl group.

The above-described subphthalocyanine compounds may be used as a colorant, alone or in combination with one or more other colorants. The subphthalocyanine compounds may be incorporated into ink compositions, which may form an ink set including yellow, blue, black, and magenta inks.

The present invention also relates to colorant compositions having improved stability, wherein the colorant comprises one or more of the above-described subphthalocyanine compounds. Desirably, one or more of the new subphthalocyanine compounds are admixed with or covalently bonded to a colorant stabilizer. The colorant stabilizer may be one or more colorant stabilizers disclosed in the following U.S. patent applications Ser. Nos. 08/563,381 filed Nov. 28, 1995, now abandoned; Ser. No. 08/589,321 filed Jan. 22, 1996, now abandoned; and Ser. No. 08/788,863 filed Jan. 23, 1997, pending; and U.S. Pat. Nos. 5,782,963; 5,855,655; 5,885,337; and 5,891,229; all of which are assigned to Kimberly Clark Worldwide, Inc., the entirety of which is incorporated herein by reference. Optionally, the new subphthalocyanine compounds may be associated with a molecular includant, chelating agent, or other material to improve solubility and/or interaction of the subphthalocyanine compound and any colorant stabilizers present. Suitable molecular includant, chelating agent, and other composition materials are also disclosed in the above-referenced U.S. Patent Applications and Patents assigned to Kimberly Clark Worldwide, Inc., the entirety of which is incorporated herein by reference.

In one embodiment of the present invention, the above-described subphthalocyanine compound is covalently bonded to a colorant stabilizer in the form of a porphine. Suitable porphines are disclosed in U.S. Pat. Nos. 5,782,963; 5,855,655; and 5,891,229; all of which are assigned to Kimberly Clark Worldwide, Inc., the entirety of which is incorporated herein by reference. Desirably, the porphine is covalently bonded to the subphthalocyanine compound at Z, Z$_1$, and/or Z$_2$. In a further embodiment of the present invention, two subphthalocyanine compounds are covalently bonded to one another. In this embodiment, it is desirable for one subphthalocyanine compound to be bonded to the other subphthalocyanine compound at Z, Z$_1$ and/or Z$_2$.

The present invention is further described by the examples, which follow. Such examples, however, are not to be construed as limiting in any way either the spirit or scope of the present invention. In the examples, all parts are parts by weight unless stated otherwise.

EXAMPLE 1

Preparation of Subphthalocyanine in Xylene

The following reaction was conducted to produce a subphthalocyanine:

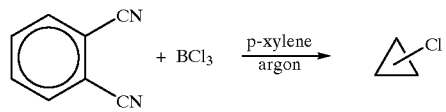

10.0 g (0.078 mole) of phthalonitrile (Aldrich Chemical Company) was added to 100 ml of p-xylene. The mixture was distilled using a Dean and Stark apparatus in order to remove any water present in the mixture. The mixture was allowed to cool to a temperature below about 50° C. The mixture was then added to a three-necked, round-bottom 250 ml flask equipped with stirrer bar, condenser, thermometer, argon bubbler, and argon inlet tube.

The mixture was heated to 50° C. Into the heated mixture was syringed 26 ml of a 1M solution containing 3.04 g (0.026 mole) of boron trichloride (Aldrich Chemical Company) in p-xylene over a period of about 2 minutes. The reaction mixture turned an orange/red color. The reaction mixture was gradually heated up to a reflux temperature of about 138° C. The reaction was monitored using HPLC analysis. Aliquots were removed during the reaction to obtain a UV spectra of each aliquot. The reaction was stopped about 35 minutes after the introduction of the boron trichloride solution.

The reaction mixture was cooled to ambient temperature and 20 ml of hexane was added to the mixture. The reaction mixture was filtered and pumped under vacuum for 4 hours at 0.01 mm Hg to remove any solvent. The reaction produced 9.9 g of a red/brown solid. The yield was 90%.

The following analytical data was measured. The solid was analyzed on a HPLC 1100 Series (Hewlett Packard) using acetonitrile and a ZORBAX™ column.

$\lambda_{max}$ (p-xylene solvent)=564 nm

TLC (silica with CHCl$_3$ as eluent) R$_f$=0.71

HPLC Retention time=5.5 min.

EXAMPLE 2

Preparation of Subphthalocyanine in Cumene

The following reaction was conducted to produce a subphthalocyanine:

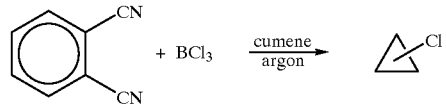

Example 1 was repeated except cumene was used as the solvent and hydrogen source, instead of p-xylene. The reaction mixture was 10.0 g (0.078 mole) of phthalonitrile (Aldrich Chemical Company), 100 ml of cumene, and 26 ml of a 1M solution containing 3.04 g (0.026 mole) of boron trichloride (Aldrich Chemical Company) in p-xylene. The reaction was stopped about 45 minutes after the introduction of the boron trichloride solution.

The reaction mixture was cooled to ambient temperature and 20 ml of hexane was added to the mixture. The reaction mixture was filtered and pumped under vacuum for 4 hours at 0.01 mm Hg to remove any solvent. The reaction produced 10.8 g of a deep red solid. The yield was 96%. The following analytical data was measured:

$\lambda_{max}$ (p-xylene solvent)=564 nm

TLC (silica with CHCl$_3$ as eluent) R$_f$=0.71

HPLC Retention time=5.5 min.

EXAMPLE 3

Preparation of Trinitrosubphthalocyanine in Cumene

The following reaction was conducted to produce a nitrite-substituted subphthalocyanine:

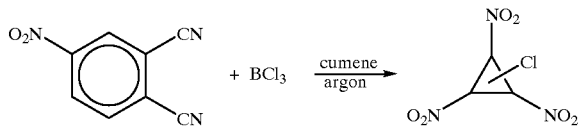

Example 2 was repeated except 4-nitrophthalonitrile was used as a reactant, in place of phthalonitrile. The reaction mixture was 10.0 g (0.058 mole) of 4-nitrophthalonitrile (Aldrich Chemical Company), 100 ml of cumene, and 19.2 ml of a 1M solution containing 2.25 g (0.019 mole) of boron trichloride (Aldrich Chemical Company) in p-xylene. The reaction was stopped about 25 minutes after the introduction of the boron trichloride solution.

The reaction mixture was cooled to ambient temperature and 20 ml of hexane was added to the mixture. The reaction mixture was filtered and pumped under vacuum for 4 hours at 0.01 mm Hg to remove any solvent. The reaction produced 10.5 g of a purple solid. The yield was 96.3%. The following analytical data was taken.

$\lambda_{max}$ (p-xylene solvent)=586 nm
TLC (silica with $CHCl_3$ as eluent) $R_f$=0.63
HPLC Retention time=4.7 min.

EXAMPLE 4

Preparation of Tri-tert-butylsubphthalocyanine in Cumene

The following reaction was conducted to produce a tert-butyl-substituted subphthalocyanine:

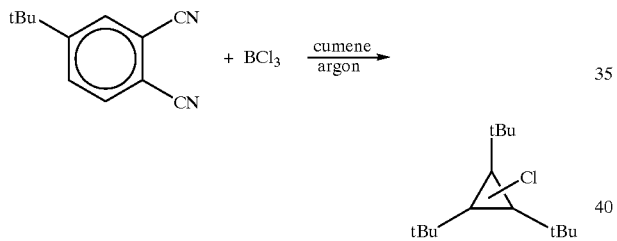

Example 2 was repeated except 4-tert-butylphthalonitrile was used as a reactant, in place of phthalonitrile. A 25 ml three-necked, round-bottom flask was used instead of the 250 ml flask used in Example 2. The reaction mixture was 1.0 g (5.4 mmole) of 4-tert-butylphthalonitrile (Aldrich Chemical Company), 10 ml of cumene, and 1.8 ml of a 1M solution containing 0.21 g (1.8 mmole) of boron trichloride (Aldrich Chemical Company) in p-xylene. The reaction was stopped about 67 minutes after the introduction of the boron trichloride solution.

The reaction mixture was cooled to ambient temperature and 2 ml of hexane was added to the mixture. The reaction mixture was pumped under vacuum for 4 hours at 0.01 mm Hg to remove any solvent. The reaction produced 1.05 g of a pink/red solid. The yield was 90%. The following analytical data was measured:

$\lambda_{max}$ (p-xylene solvent)=569 nm
HPLC Retention time=18.9 min.

EXAMPLE 5

Preparation of Dichlorosubphthalocyanine in Cumene

The following reaction was conducted to produce a chlorine-substituted subphthalocyanine:

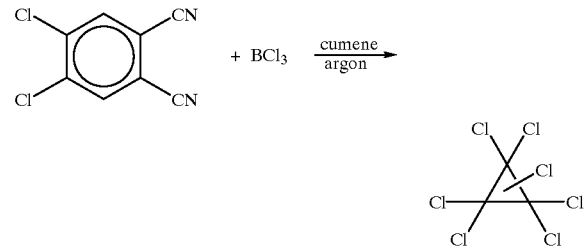

Example 2 was repeated except 4,5-dichlorophthalonitrile was used as a reactant, in place of phthalonitrile. The reaction mixture was 10.0 g (0.051 mole) of 4,5-dichlorophthalonitrile (Aldrich Chemical Company), 100 ml of cumene, and 16.9 ml of a 1M solution containing 2.0 g (0.017 mole) of boron trichloride (Aldrich Chemical Company) in p-xylene. The reaction mixture turned red and then deep red/blue during heating up to a reflux temperature of about 150° C. The reaction was stopped about 60 minutes after the introduction of the boron trichloride solution.

The reaction mixture was cooled to ambient temperature and 60 ml of hexane was added to the mixture. The reaction mixture was filtered and pumped under vacuum for 4 hours at 0.01 mm Hg to remove any solvent. The reaction produced 10.1 g of a red/purple solid. The yield was 92%.

The following analytical data was taken.

$\lambda_{max}$ (p-xylene solvent)=574 nm
HPLC Retention time=25.5 min.

EXAMPLE 6

Preparation of Tetra-fluorosubphthalocyanine in Cumene

The following reaction was conducted to produce a fluorine-substituted subphthalocyanine:

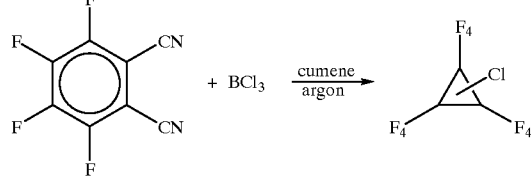

Example 2 was repeated except 3,4,5,6-tetrafluorophthalonitrile was used as a reactant, in place of phthalonitrile. The reaction mixture was 10.0 g (0.050 mole) of 3,4,5,6-tetrafluorophthalonitrile (Aldrich Chemical Company), 100 ml of cumene, and 16.7 ml of a 1M solution containing 1.95 g (0.017 mole) of boron trichloride (Aldrich Chemical Company) in p-xylene. The reaction was stopped about 30 minutes after the introduction of the boron trichloride solution.

The reaction mixture was cooled to ambient temperature and 60 ml of hexane was added to the mixture. The reaction mixture was filtered and pumped under vacuum for 4 hours at 0.01 mm Hg to remove any solvent. The reaction produced 10.5 g of a red/purple solid. The yield was 90%.

The following analytical data was taken.

$\lambda_{max}$ (p-xylene solvent)=577 nm
HPLC Retention time=4.4 min.

EXAMPLE 7

Preparation of Tetrachlorosubphthalocyanine in Cumene

The following reaction was conducted to produce a chlorine-substituted subphthalocyanine:

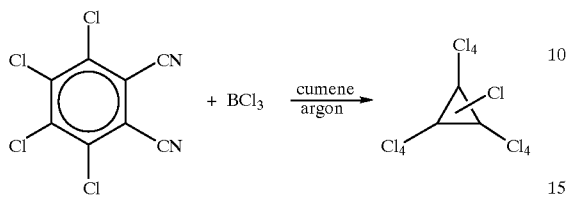

Example 2 was repeated except 3,4,5,6-tetrachlorophthalonitrile was used as a reactant, in place of phthalonitrile. The reaction mixture was 10.0 g (0.038 mole) of 3,4,5,6-tetrachlorophthalonitrile (Aldrich Chemical Company), 100 ml of cumene, and 12.5 ml of a 1M solution containing 1.47 g (0.012 mole) of boron trichloride (Aldrich Chemical Company) in p-xylene. The reaction was stopped about 80 minutes after the introduction of the boron trichloride solution.

The reaction mixture was cooled to ambient temperature and 60 ml of hexane was added to the mixture. A precipitate did not form so the reaction mixture was pumped under vacuum for 4 hours at 0.01 mm Hg and in a water bath at 50° C. to remove any solvent. The reaction produced 9.6 g of a solid. The yield was 93%.

The following analytical data was taken.

$\lambda_{max}$ (p-xylene solvent)=593 nm

HPLC Retention time=26.0 min.

EXAMPLE 8

Preparation of a "Capped" Trinitrosubphthalocyanine

The following reaction was conducted to produce a capped trinitrosubphthalocyanine:

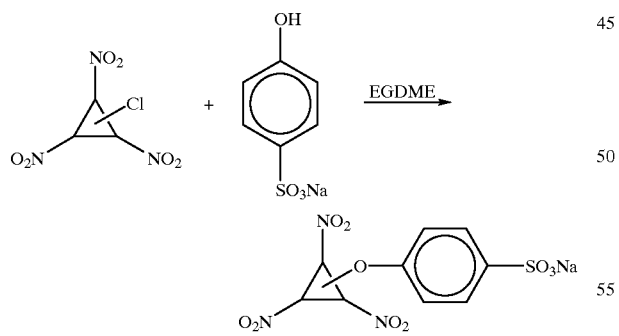

Into a 250 ml round-bottom flask equipped with magnetic stirrer bar was placed 2.0 g (3.54 mmole) of trinitrosubphthalocyanine from Example 3; 0.69 g (3.54 mmole) of 4-hydroxybenzene sulphonic acid, sodium salt (Aldrich Chemical Company); and 100 ml of ethylene glycol dimethyl ether (EGDME) (Aldrich Chemical Company). The mixture was gradually heated up to a reflux temperature of about 85° C. The mixture was heated at reflux for about 16 hours.

The reaction mixture was cooled to ambient temperature. The reaction mixture was pumped under vacuum for 4 hours at 0.01 mm Hg to remove any solvent. The reaction produced 2.1 g of a solid. The yield was 84%.

EXAMPLE 9

Preparation of a "Capped" Dichlorosubphthalocyanine

The following reaction was conducted to produce a capped dichlorosubphthalocyanine:

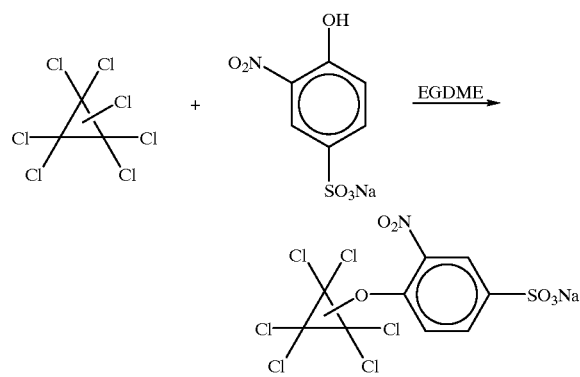

Into a 250 ml round-bottom flask equipped with magnetic stirrer bar was placed 2.0 g (3.5 mmole) of dichlorosubphthalocyanine from Example 5; 0.84 g (3.5 mmole) of 4-hydroxy-3-nitrobenzene sulphonic acid, sodium salt (Aldrich Chemical Company); and 100 ml of ethylene glycol dimethyl ether (Aldrich Chemical Company). The mixture was gradually heated up to a reflux temperature of about 85° C. The mixture was heated at reflux for about 16 hours.

The reaction mixture was cooled to ambient temperature. The reaction mixture was pumped under vacuum for 4 hours at 0.01 mm Hg to remove any solvent. The reaction produced 2.4 g of a red/brown solid. The yield was 89%.

EXAMPLE 10

Preparation of a Di-Subphthalocyanine in Cumene

The following reaction was conducted to produce a dis-ubphthalocyanine:

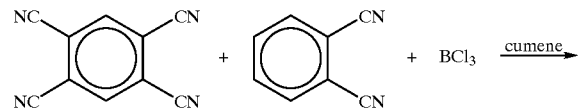

-continued

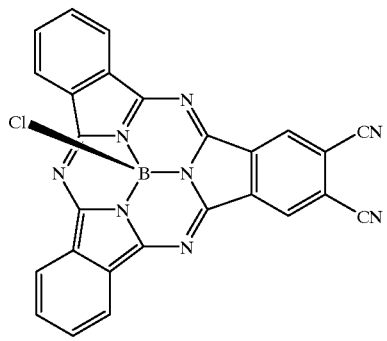

+

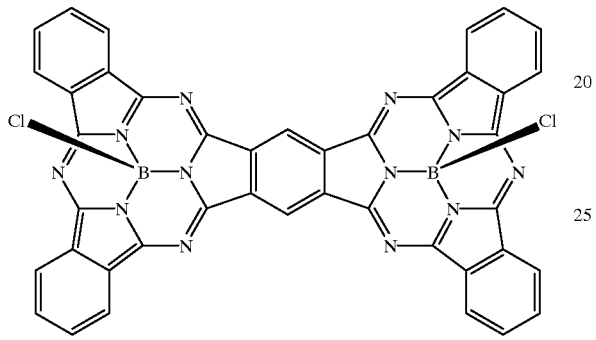

2.0 g (0.011 mole) of tetracyanobenzene (Aldrich Chemical Company) and 6.1 g (0.044 mole) of phthalonitrile (Aldrich Chemical Company) were added to 80 ml of cumene. The mixture was distilled using a Dean and Stark apparatus in order to remove any water present in the mixture. The mixture was allowed to cool to a temperature below about 60° C. The mixture was then added to a three-necked, round-bottom 2000 ml flask equipped with stirrer bar, condenser, thermometer, argon bubbler, and argon inlet tube.

The mixture was heated to 60° C. Into the heated mixture was syringed 11 ml of a 1M solution containing 1.3 g (0.011 mole) of boron trichloride (Aldrich Chemical Company) in p-xylene over a period of about 3 minutes. The reaction mixture turned a red/blue color. The reaction mixture was gradually heated up to a reflux temperature of about 150° C. The reaction mixture was monitored using HPLC analysis. Aliquots were removed during the reaction to obtain a UV spectra of each aliquot. The reaction was stopped about 20 minutes after the introduction of the boron trichloride solution.

The reaction mixture was cooled to ambient temperature. The reaction mixture was pumped under vacuum for 4 hours at 0.01 mm Hg to remove any solvent. The reaction produced 9.9 g of a red/brown solid. The yield was 98%.

EXAMPLE 10

Measurement of Subphth.-Lightfastness Values for a Variety of Subphthalocyanine Compound Solutions A variety of subphthalocyanines were prepared as described above. The subphthalocyanines were dissolved in o-xylene to form stock solutions having a subphthalocyanine concentration of $5 \times 10^{-5}$ M. Each stock solution was split into four separate 50 ml. solutions and placed in Pyrex conical flasks labeled A, B, C, and D. The flasks were sealed with aluminum foil.

Five milliliters of distilled water was added to Samples B and D of each set. Samples A and B were placed on a laboratory benchtop about six feet from fluorescent lamps (i.e., Sylvania Cool White, 115 W, Model No. F48T12), which remained on 24 hours/day. Samples C and D were placed in a dark refrigerator at 10° C. Each day sample aliquots were removed from each sample to measure the absorption of the sample. Subphth-Lightfastness Test values were determined for each sample for each subphthalocyanine solution at 21 hours, 48 hours, and 144 hours. The results are given in Table 1 below.

The subphthalocyanines tested had the following formula, wherein "R" varied as shown in Table 1.

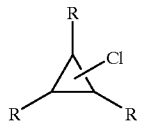

TABLE 1

Subphth-Lightfastness Test Values For Subphthalocyanine Compounds

| Subphthalocyanine Substituents | | | Subphth-Lightfastness Test Values (% ΔA) | | |
|---|---|---|---|---|---|
| "R" | "Z" | Sample | 21 Hours | 48 Hours | 144 Hours |
| Cl$_4$ | Cl | A | 3 | 3 | 9 |
| Cl$_4$ | Cl | B | 0 | 2 | 12 |
| Cl$_4$ | Cl | C | 2 | 2 | 2 |
| Cl$_4$ | Cl | D | 0 | 2 | 2 |
| F$_4$ | Cl | A | 8 | 12 | 19 |
| F$_4$ | Cl | B | 8 | 13 | 26 |
| F$_4$ | Cl | C | 6 | 7 | 8 |
| F$_4$ | Cl | D | 6 | 8 | 12 |
| Cl$_2$ | Cl | A | 11 | 16 | 31 |
| Cl$_2$ | Cl | B | 9 | 13 | 36 |
| Cl$_2$ | Cl | C | 6 | 8 | 10 |
| Cl$_2$ | Cl | D | 10 | 13 | 14 |
| NO$_2$ | Cl | A | 7 | 14 | 40 |
| NO$_2$ | Cl | B | 12 | 22 | 48 |
| NO$_2$ | Cl | C | 7 | 7 | 8 |
| NO$_2$ | Cl | D | 10 | 10 | 12 |
| H | Cl | A | 12 | 22 | 57 |
| H | Cl | B | 5 | 16 | 31 |
| H | Cl | C | 0 | 0 | 0 |
| H | Cl | D | 0 | 0 | 0 |
| H | OPh | A | 7 | 14 | 39 |
| H | OPh | B | 12 | 22 | 41 |
| H | OPh | C | 0 | 0 | 0 |
| H | OPh | D | 0 | 2 | 6 |

EXAMPLE 11

Preparation of Unsymmetrical Subphthalocyanine Compounds in Cumene

The following reaction was conducted to produce unsymmetrical subphthalocyanine compounds at the given yield:

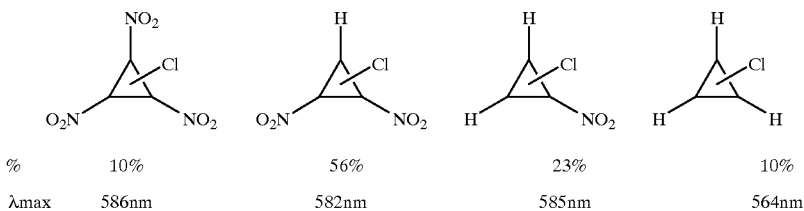

| % | 10% | 56% | 23% | 10% |
| λmax | 586nm | 582nm | 585nm | 564nm |

3.3 g (0.019 mole) of 4-nitrophthalonitrile (Aldrich Chemical Company) and 4.9 g (0.038 mole) of phthalonitrile (Aldrich Chemical Company) were added to 80 ml of cumene. The mixture was distilled using a Dean and Stark apparatus in order to remove any water present in the mixture. The mixture was allowed to cool to a temperature below about 50° C. The mixture was then added to a three-necked, round-bottom 250 ml flask equipped with stirrer bar, condenser, thermometer, argon bubbler, and argon inlet tube.

The mixture was heated to 50° C. Into the heated mixture was syringed 19.2 ml of a 1M solution (0.019 mole) of boron trichloride (Aldrich Chemical Company) in cumene over a period of about 2 minutes. The reaction mixture was gradually heated up to a reflux temperature of about ° C. and held at this temperature for about 45 minutes. The reaction was monitored using HPLC analysis.

The product was analyzed on a HPLC 1100 Series (Hewlett Packard) using acetonitrile and a C-18 HYPERSIL™ column. The HPLC spectra showed four peaks around the 5 min retention area. The resulting spectra was compared to reference spectra for various compounds. The four peaks corresponded to peaks on the spectra of the four compounds shown above. The weight percent of each compound was calculated and found to be 10 wt % A, 56 wt % B, 23 wt % C, and 10 wt % D as shown above.

6.6 g (0.038 mole) of 4-nitrophthalonitrile (Aldrich Chemical Company) and 2.4 g (0.019 mole) of phthalonitrile (Aldrich Chemical Company) were added to 80 ml of cumene. The mixture was distilled using a Dean and Stark apparatus in order to remove any water present in the mixture. The mixture was allowed to cool to a temperature below about 50° C. The mixture was then added to a three-necked, round-bottom 250 ml flask equipped with stirrer bar, condenser, thermometer, argon bubbler, and argon inlet tube.

The mixture was heated to 50° C. Into the heated mixture was syringed 19.2 ml of a 1M solution (0.019 mole) of boron trichloride (Aldrich Chemical Company) in cumene over a period of about 2 minutes. The reaction mixture was gradually heated up to a reflux temperature of about ° C. and held at this temperature for about 45 minutes. The reaction was monitored using HPLC analysis.

The product was analyzed on a HPLC 1100 Series (Hewlett Packard) using acetonitrile and a C-18 HYPERSIL™ column. The HPLC spectra showed four peaks around the 5 min retention area. The resulting spectra was compared to reference spectra for various compounds. The four peaks corresponded to peaks on the spectra of the four compounds shown above. The weight percent of each compound was calculated and found to be 33 wt % A, 54 wt % B, 13 wt % C, and <1 wt % D as shown above.

EXAMPLE 12

Preparation of Unsymmetrical Subphthalocyanine Compounds in Cumene

The following reaction was conducted to produce unsymmetrical subphthalocyanine compounds at the given yield:

EXAMPLE 13

Preparation of Unsymmetrical Subphthalocyanine Compounds in Cumene

The following reaction was conducted to produce unsymmetrical subphthalocyanine compounds at the given yield:

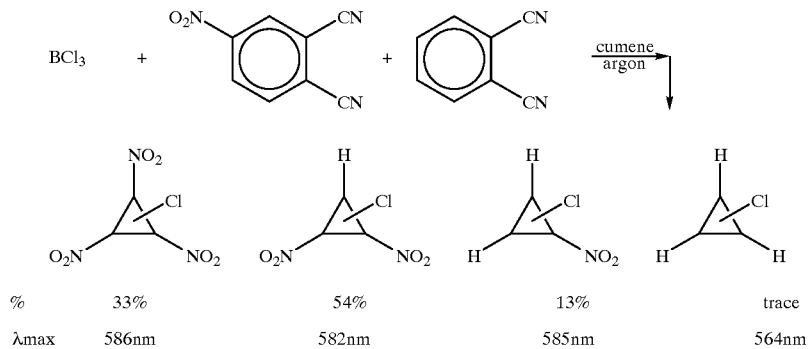

| % | 33% | 54% | 13% | trace |
| λmax | 586nm | 582nm | 585nm | 564nm |

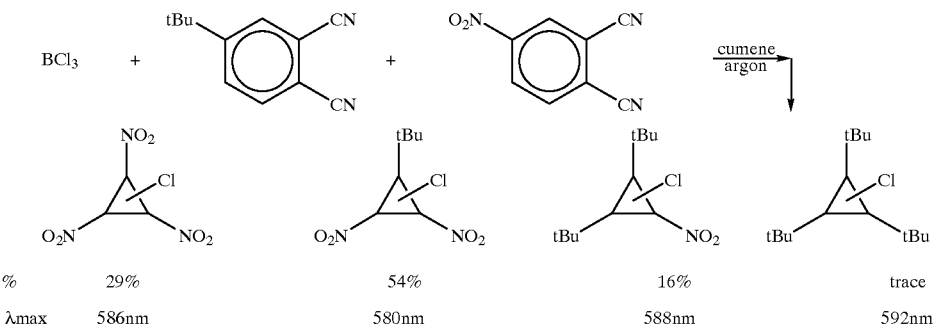

| % | 29% | 54% | 16% | trace |
|---|---|---|---|---|
| λmax | 586nm | 580nm | 588nm | 592nm |

3.50 g (0.019 mole) of 4-tert-butylphthalonitrile (Aldrich Chemical Company) and 6.57 g (0.038 mole) of 4-nitrophthalonitrile (Aldrich Chemical Company) were added to 80 ml of cumene. The mixture was distilled using a Dean and Stark apparatus in order to remove any water present in the mixture. The mixture was allowed to cool to a temperature below about 50° C. The mixture was then added to a three-necked, round-bottom 250 ml flask equipped with stirrer bar, condenser, thermometer, argon bubbler, and argon inlet tube.

The mixture was heated to 50° C. Into the heated mixture was syringed 19.2 ml of a 1M solution (0.019 mole) of boron trichloride (Aldrich Chemical Company) in cumene over a period of about 2 minutes. The reaction mixture was gradually heated up to a reflux temperature of about 138° C. and held at this temperature for about 30 minutes. The reaction was monitored using HPLC analysis.

The product was analyzed on a HPLC 1100 Series (Hewlett Packard) using acetonitrile and a C-18 HYPERSIL™ column. The HPLC spectra showed four peaks around the 5 min retention area. The resulting spectra was compared to reference spectra for various compounds. The four peaks corresponded to peaks on the spectra of the four compounds shown above. The weight percent of each compound was calculated and found to be 29 wt % A, 54 wt % B, 16 wt % C, and <1 wt % D as shown above.

EXAMPLE 14

Preparation of Unsymmetrical Subphthalocyanine Compounds in a Cumene/Xylene Mixture The following reaction was conducted to produce unsymmetrical subphthalocyanine compounds:

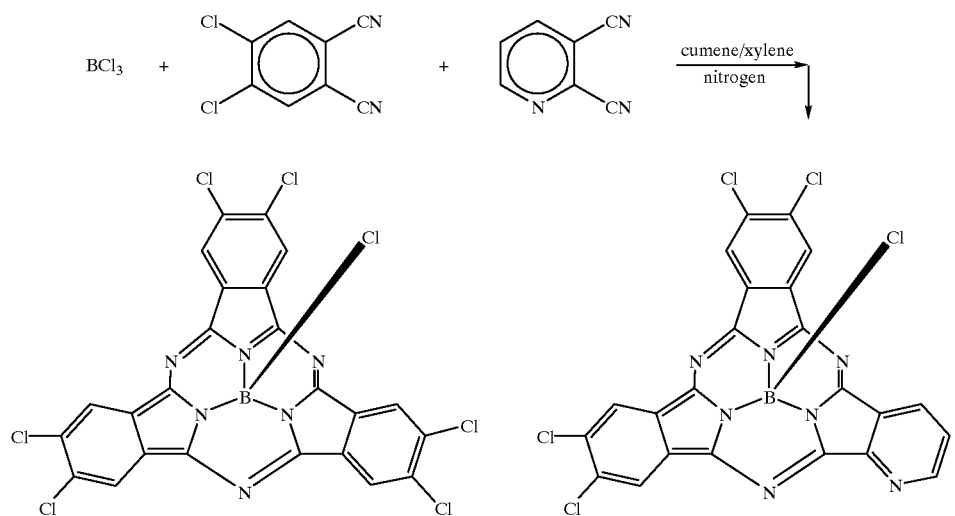

1.50 g (7.8 mmole) of 2,3-dichlorophthalonitrile (Aldrich Chemical Company) and 0.50 g (3.9 mmole) of pyridine-2,3-dicarbonitrile (TCI America, Portland, OR) were added to a mixture of 3 ml of cumene and 27 ml of xylene. The mixture was distilled for about 40 minutes using a Dean and Stark apparatus in order to remove any water present in the mixture. The mixture was allowed to cool to a temperature below about 50° C. and the trap was removed.

The mixture was then added to a three-necked, round-bottom 250 ml flask equipped with stirrer bar, condenser, thermometer, argon bubbler, and argon inlet tube. The mixture was heated to 50° C. under a nitrogen blanket. Into the heated mixture was syringed 11.7 ml of a 1M solution (11.7 mmole) of boron trichloride (Aldrich Chemical Company) in cumene over a period of about 5 minutes. The reaction mixture was gradually heated up to a reflux temperature of about 138° C. and held at this temperature for about 60 minutes. The reaction was monitored using HPLC analysis.

The product was analyzed on a HPLC 1100 Series (Hewlett Packard) using acetonitrile and a C-18 HYPER- SIL™ column. The HPLC spectra showed two peaks, one at a retention time of 8.1 minutes and one at 25.4 minutes. The resulting spectra was compared to reference spectra for various compounds. The two peaks corresponded to peaks on the spectra of hexachlorosubphthalocyanine and the above unsymmetrical subphthalocyanine compound. The weight percent hexachlorosubphthalocyanine was found to be 77 wt % and the weight percent of the unsymmetrical subphthalocyanine compound was found to be about 15 wt %.

The reaction mixture was cooled to ambient temperature and 30 ml of hexane was added to the reaction mixture. The mixture was filtered. The solid was washed with hexane and then dried in a vacuum oven at ambient temperature and 0.01 mmHg for about 4 hours. The yield was 2.0 g of product.

EXAMPLE 15

Preparation of a "Capped" Subphthalocyanine

The following reaction was conducted to produce a capped dichlorosubphthalocyanine:

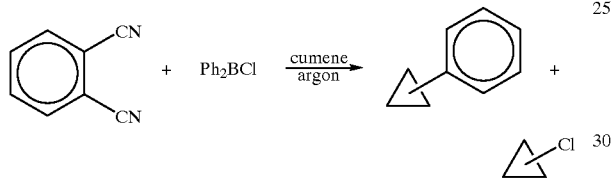

Into a 250 ml round-bottom flask equipped with magnetic stirrer bar was placed 3.8 g (0.3 mole) of phthalonitrile (Aldrich Chemical Company) and 30 ml of cumene (Aldrich Chemical Company) under an argon atmosphere. By syringe, 2.0 g (0.01 mole) of chlorodiphenylboron (Aldrich Chemical Company) was added. The mixture was gradually heated up to a reflux temperature of about 138° C. The mixture was heated at reflux for about 90 minutes.

The reaction mixture was cooled to room temperature and 40 ml of hexane was added to the mixture. The precipitate was filtered. The product was analyzed on a HPLC 1100 Series (Hewlett Packard) using acetonitrile and a C-18 HYPERSIL™ column. HPLC analysis showed the product to be 75 wt % of the phenyl capped subphthalocyanine compound and 25 wt % of the chlorine capped subphthalocyanine compound. The yield of the reaction was 3.1 g.

The subphthalocyanine compounds were separated by column chromatography using neutral alumina with a 50:50 mixture by volume of methylene chloride and toluene as an eluent.

EXAMPLE 16

Preparation of a Symmetrical Subphthalocyanine

The following reaction was conducted to produce a subphthalocyanine:

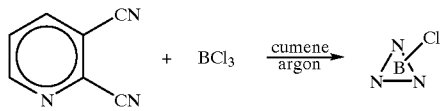

-continued

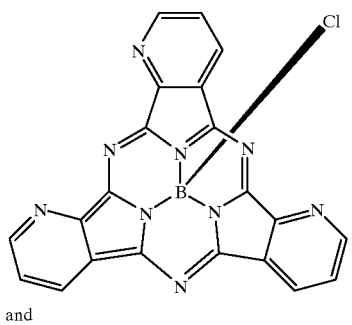

and

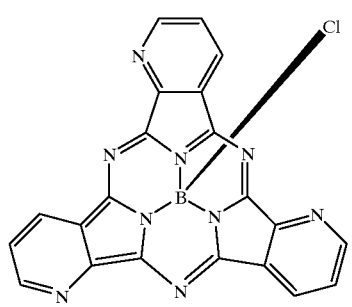

Into a 250 ml round-bottom flask flushed with argon and equipped with magnetic stirrer bar was placed 2.0 g (0.155 mole) of pyridine-2,3-dicarbonitrile (TCI America, Portland, OR) and 30 ml of cumene (Aldrich Chemical Company). By syringe, 1.8 g (0.0155 mole) of trichloroboron (Aldrich Chemical Company) in xylene was added to the mixture. The mixture turned yellow and then a brown/red color at room temperature. The mixture was gradually heated up to a temperature of about 80° C. and held at this temperature for about 30 minutes.

The reaction mixture was cooled to room temperature and the precipitate was filtered. The product was washed with hexane. The yield of the reaction was 1.5 g (Actual yield 71%).

EXAMPLE 17

Preparation of a Mixture of Symmetrical and Unsymmetrical Subphthalocyanine Compounds The following reaction was conducted to produce a mixture of symmetrical and unsymmetrical subphthalocyanine compounds:

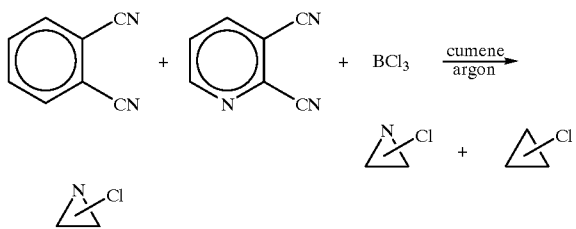

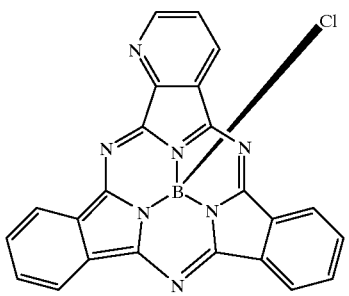

Into a 250 ml round-bottom flask flushed with argon and equipped with magnetic stirrer bar was placed 2.0 g (15.5 mmole) of phthalonitrile (Aldrich Chemical Company), 1.0 g (7.8 mmole) of pyridine-2,3-dicarbonitrile (TCI America, Portland, OR) and 30 ml of cumene (Aldrich Chemical Company). By syringe, 1.8 g (15.5 mmole) of trichloroboron (Aldrich Chemical Company) in xylene was added to the mixture. The mixture was gradually heated up to a reflux temperature of about 138° C. The mixture was heated at reflux for about 45 minutes and then cooled to room temperature.

30 ml of hexane was added to the reaction mixture. The precipitate was filtered and washed with hexane. The yield of the reaction was 2.5 g.

HPLC analysis showed the product to be a mixture of 18 wt % of the symmetrical subphthalocyanine compound and 82 wt % of the unsymmetrical subphthalocyanine compound.

EXAMPLE 18

Mass Spectroscopy Analysis of Selected Subphthalocyanine Compounds

Using the techniques in the examples above, a number of subphthalocyanine compounds were produced. The compounds were analyzed using two different mass spectrometers. The following compounds were analyzed by atmospheric pressure chemical ionization (APCI) on a Micromass Quattro II Triple Quadrupole Mass Spectrometer:

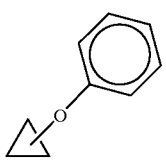
489

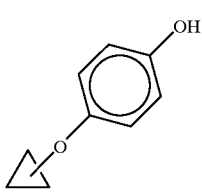
505

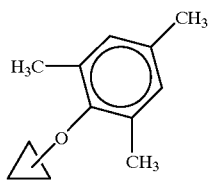
531

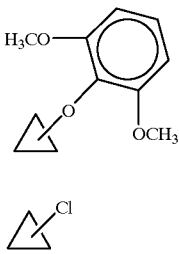
548

413

The following compounds were analyzed using a Thermoquest LCQ Mass Spectrometer:

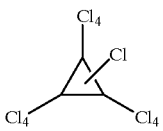
838.8

414

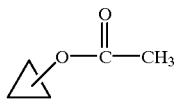
454

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An ink composition comprising a subphthalocyanine compound having a Subphth-Lightfastness Test Value of less than about 15% and having the following general formula:

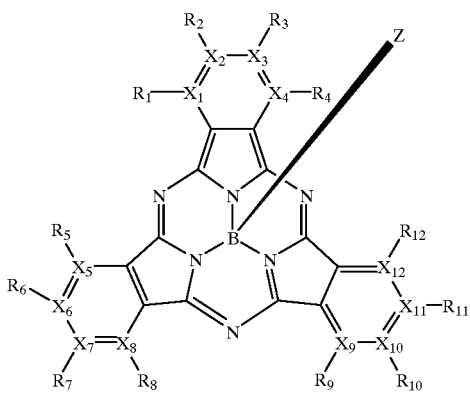

wherein $X_1$ to $X_{12}$ each independently represent carbon or nitrogen; $R_1$ to $R_{12}$ and Z each independently represent —H, a halogen, an alkyl group, a substituted alkyl group, an aryl group, a substituted aryl group, an alkoxide group, a phenoxy group, a substituted phenoxy group, an alkyl sulfide, an aryl sulfide, a nitrogen-containing group, a sulfonic acid, a sulfur-containing group, a lanthanide-containing group, or an ester group; and wherein when any one of $X_1$ to $X_{12}$ is nitrogen, the corresponding $R_1$ to $R_{12}$ represents the pair of electrons on the nitrogen atom.

2. The ink composition of claim 1, wherein $R_1$ to $R_{12}$ each independently represent —H, chlorine, bromine, fluorine, iodine, a tert-butyl group, —$NO_2$, -$SO_3H$, —$SO_3Na$, —$SO_3Cl$, —$SO_3^-pyH^+$, or a Eu-containing moiety.

3. The ink composition of claim 2, wherein $R_1$ to $R_{12}$ each independently represent —H, chlorine, bromine, fluorine, iodine.

4. The ink composition of claim 1, wherein Z represents a moiety selected from the group consisting of:

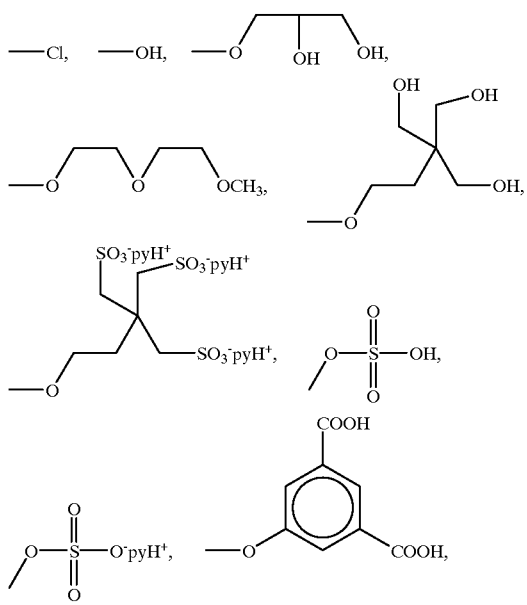

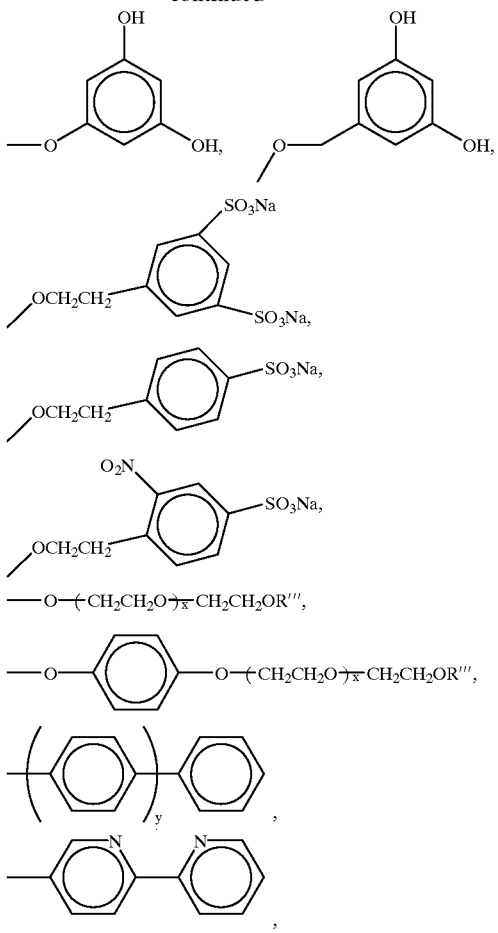

and

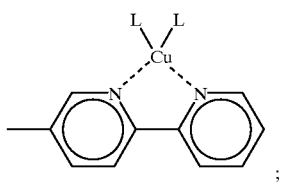

where x is an integer from 3 to 30, y is from 0 to 6, R''' is a hydrogen or an alkyl group having up to six carbon atoms, and L is acetate; a halogen; ethylene diamine; compounds having the following structure, $H_2N(CH_2)_xNH_2$, wherein x is from 2 to 8; propionate; nitrate; or oxalate.

5. The ink composition of claim 1, wherein Z represents —Cl, a phenyl group, or —OR', where R' represent an alkyl, substituted alkyl, aryl, or substituted aryl.

6. An ink set comprising two or more inks, wherein at least one ink comprises the ink composition of claim 1.

7. The ink set of claim 6, wherein the ink set further comprises a yellow ink, a blue ink, and a black ink.

8. A subphthalocyanine compound having a Subphth-Lightfastness Test Value of less than about 15%, and having a general formula:

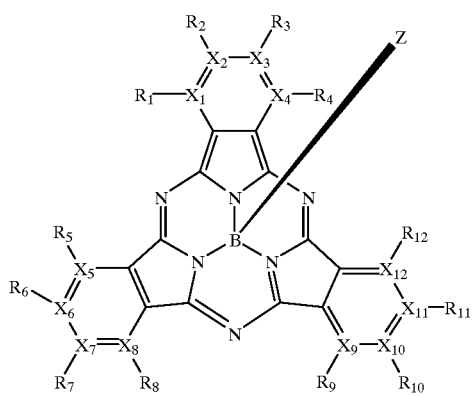

wherein $X_1$ to $X_{12}$ each independently represent carbon or nitrogen; $R_1$ to $R_{12}$ and Z each independently represent —H, a halogen, an alkyl group, a substituted alkyl group, an aryl group, a substituted aryl group, an alkoxide group, a phenoxy group, a substituted phenoxy group, an alkyl sulfide, an aryl sulfide, a nitrogen-containing group, a sulfonic acid, a lanthanide-containing group, or an ester group; and wherein when any one of $X_1$ to $X_{12}$ is nitrogen, the corresponding $R_1$ to $R_{12}$ represents the pair of electrons on the nitrogen atom.

9. The subphthalocyanine compound of claim 8, wherein the compound has a Subphth-Lightfastness Test Value of less than about 12%.

10. The subphthalocyanine compound of claim 9, wherein the compound has a Subphth-Lightfastness Test Value of less than about 10%.

11. The subphthalocyanine compound of claim 8, wherein $R_1$ to $R_{12}$ each independently represent —H, chlorine, bromine, fluorine, iodine, a tert-butyl group, -$NO_2$, —$SO_3H$, —$SO_3Na$, —$SO_3Cl$, —$SO_3^-pyH^+$, or a Eu-containing moiety.

12. The subphthalocyanine compound of claim 8, wherein $R_1$ to $R_{12}$ each independently represent —H, chlorine, bromine, fluorine, or iodine.

13. The subphthalocyanine compound of claim 8, wherein Z represents a moiety selected from the group consisting of:

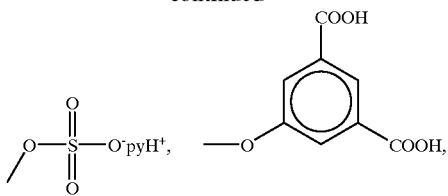

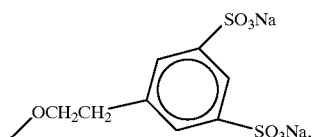

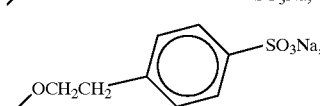

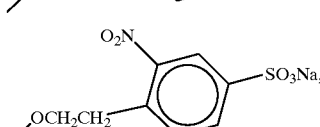

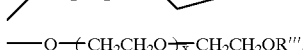

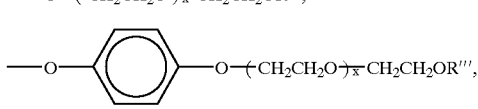

and

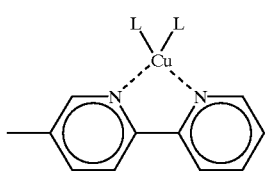

;

where x is an integer from 3 to 30, y is from 0 to 6, R''' is a hydrogen or an alkyl group having up to six carbon atoms, and L is acetate, propionate, nitrate, or oxalate.

14. The subphthalocyanine compound of claim 13, wherein Z represents —Cl, a phenyl group, or —OR', where R' represent an alkyl, substituted alkyl, aryl, or substituted aryl.

15. An ink composition comprising the subphthalocyanine compound of claim 8.

16. An ink set comprising at least two inks, wherein at least one ink comprises the ink composition of claim 15.

17. A subphthalocyanine compound containing one or more moieties having a spin-orbital coupling constant, 4l, of greater than about 500, wherein the compound has a general formula:

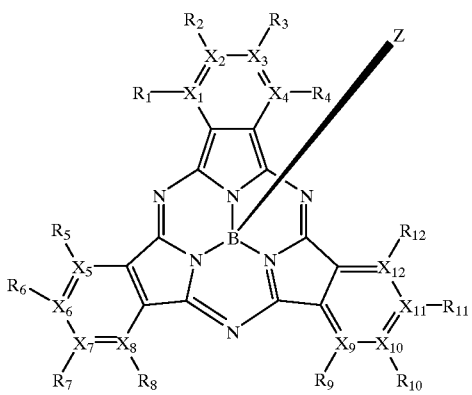

wherein $X_1$ to $X_{12}$ each independently represent carbon or nitrogen; $R_1$ to $R_{12}$ and Z each independently represent —H, a halogen, an alkyl group, a substituted alkyl group, an aryl group, a substituted aryl group, an alkoxide group, a phenoxy group, a substituted phenoxy group, an alkyl sulfide, an aryl sulfide, a nitrogen-containing group, a sulfonic acid, a lanthanide-containing group, or an ester group; and wherein when any one of $X_1$ to X12 is nitrogen, the corresponding $R_1$ to $R_{12}$ represents the pair of electrons on the nitrogen atom.

18. The subphthalocyanine compound of claim 17, wherein the compound containing one or more moieties having a spin-orbital coupling constant, $\iota_f$, of greater than about 1000.

19. The subphthalocyanine compound of claim 18, wherein the compound containing one or more moieties having a spin-orbital coupling constant, $\iota_f$, of greater than about 1400.

20. A method of making a subphthalocyanine compound, wherein the method comprises reacting one or more first reactants with one or more hydrogen-donating solvents, and wherein the method takes place at a temperature below about 180° C., and produces the subphthalocyanine compound at a reaction yield of greater than about 50%.

21. A method of making a subphthalocyanine compound, wherein the method takes place at a temperature below about 180° C., and produces the subphthalocyanine compound at a reaction yield of greater than about 80%.

22. The method of claim 21, wherein the yield is greater than about 90%.

23. The method of claim 22, wherein the yield is greater than about 94%.

24. The method of claim 22, wherein the method comprises reacting one or more first reactants with one or more hydrogen-donating solvents.

25. The method of claim 24, wherein the one or more first reactants comprise phthalonitrile, substituted phthalonitriles, pyridine-2,3-dicarbonitrile, substituted pyridine-2,3-dicarbonitriles, pyridine-3,4-dicarbonitrile, substituted pyridine-3,4-dicarbonitriles, pyrazine-2,3-dicarbonitrile, substituted pyrazine-2,3-dicarbonitriles, or a combination thereof.

26. The method of claim 24, wherein the one or more hydrogen-donating solvents comprise substituted aromatic compounds, cyclohexadiene, alcohols, ethers, or a combination thereof.

27. The method of claim 26, wherein the one or more hydrogen-donating solvents comprise o-xylene, m-xylene, p-xylene, toluene, a substituted benzene wherein the substituent comprises a hydrogen-containing moiety, 2-propanol, petroleum ether, tetrahydrofuran, dioxane, tetralene, or a combination thereof.

28. The method of claim 20, wherein the compound has a general formula:

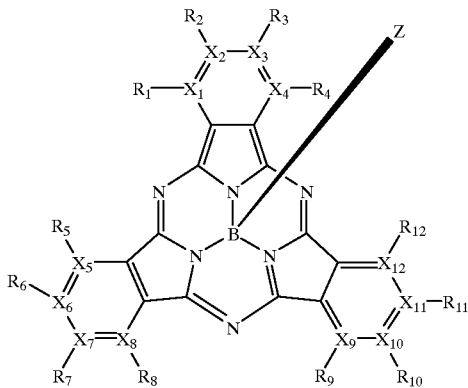

wherein $X_1$ to $X_{12}$ each independently represent carbon or nitrogen; $R_1$ to $R_{12}$ and Z each independently represent —H, a halogen, an alkyl group, a substituted alkyl group, an aryl group, a substituted aryl group, an alkoxide group, a phenoxy group, a substituted phenoxy group, an alkyl sulfide, an aryl sulfide, a nitrogen-containing group, a sulfonic acid, a sulfur-containing group, a lanthanide-containing group, or an ester group; and wherein when any one of $X_1$ $X_{12}$ is nitrogen, the corresponding $R_1$ to $R_{12}$ represents the pair of electron on the nitrogen atom.

29. A subphthalocyanine compound formed by the method of claim 20.

* * * * *